United States Patent
Shipp et al.

(10) Patent No.: US 10,519,238 B2
(45) Date of Patent: Dec. 31, 2019

(54) ANTI-GALECTIN-1 MONOCLONAL ANTIBODIES AND FRAGMENTS THEREOF

(71) Applicant: Dana-Farber Cancer Institute, Inc., Boston, MA (US)

(72) Inventors: Margaret A. Shipp, Wellesley, MA (US); Jing Ouyang, Sharon, MA (US); Scott J. Rodig, Westwood, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/907,362

(22) PCT Filed: Jul. 23, 2014

(86) PCT No.: PCT/US2014/047783
§ 371 (c)(1),
(2) Date: Jan. 25, 2016

(87) PCT Pub. No.: WO2015/013388
PCT Pub. Date: Jan. 29, 2015

(65) Prior Publication Data
US 2016/0168236 A1 Jun. 16, 2016

Related U.S. Application Data

(60) Provisional application No. 61/911,031, filed on Dec. 3, 2013, provisional application No. 61/857,839, filed on Jul. 24, 2013.

(51) Int. Cl.
| | | |
|---|---|---|
| *C07K 16/00* | (2006.01) | |
| *G01N 33/53* | (2006.01) | |
| *C07K 16/28* | (2006.01) | |
| *G01N 33/574* | (2006.01) | |
| *C07K 16/18* | (2006.01) | |
| *G01N 33/577* | (2006.01) | |
| *A61K 39/00* | (2006.01) | |
| *G01N 33/68* | (2006.01) | |

(52) U.S. Cl.
CPC ...... *C07K 16/2851* (2013.01); *A61K 39/0005* (2013.01); *C07K 16/18* (2013.01); *G01N 33/577* (2013.01); *G01N 33/57484* (2013.01); *G01N 33/6854* (2013.01); *A61K 2039/505* (2013.01); *C07K 2317/33* (2013.01); *C07K 2317/34* (2013.01); *C07K 2317/565* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,890,531 B1 | 5/2005 | Horie et al. |
| 8,968,740 B2 | 3/2015 | Shipp et al. |
| 9,206,427 B2 | 12/2015 | Shipp et al. |
| 2007/0269442 A1 | 11/2007 | Webber et al. |
| 2009/0191182 A1 | 7/2009 | Shipp et al. |
| 2010/0080794 A1 | 4/2010 | Tsuji et al. |
| 2010/0297664 A1 | 11/2010 | Wadhwa et al. |
| 2013/0011409 A1 | 1/2013 | Shipp et al. |
| 2013/0065258 A1 | 3/2013 | Watanabe et al. |

FOREIGN PATENT DOCUMENTS

| | | |
|---|---|---|
| WO | WO 1989/000581 | 1/1989 |
| WO | WO-2006/108474 A2 | 10/2006 |
| WO | WO-2007/126439 A2 | 11/2007 |
| WO | WO-2011/060272 A2 | 5/2011 |
| WO | WO-2011/157713 A2 | 12/2011 |
| WO | WO-2015/013388 A2 | 1/2015 |
| WO | WO-2015/13389 A2 | 1/2015 |

OTHER PUBLICATIONS

Rudikoff et al, Proc. Natl. Acad. Sci. USA, 79(6):1979-1983, Mar. 1982.*
Colman P. M., Research in Immunology, 145:33-36, 1994.*
Alves et al., "Significance of galectins-1, -3, -4 and -7 in the progression of squamous cell carcinoma of the tongue," Pathology Res. Pract. 207:236-240 (2011).
Chen et al., "PD-L1 Expression Is Characteristic of a Subset of Aggressive B-cell Lymphomas and Virus-Associated Malignancies," Clin. Cancer Res. 19(13):3462-3473 (2013).
Chung et al., "Proteomic Analysis to Identify Biomarker Proteins in Pancreatic Ductal Adenocarcinoma," ANZ J. Surg. 78:245-251 (2008).
Chung et al., "Galectin-1 Promotes Lung Cancer Progression and Chemoresistance by Upregulating p38 MAPK, ERK, and Cyclooxygenase-2," Clin. Cancer Res. 18:4037-4047 (2012).
Croci et al., "Disrupting galectin-1 interactions with N-glycans suppresses hypoxia-driven angiogenesis and tumorigenesis in Kaposi's sarcoma," J. Exp. Med. 209:1985-2000 (2012).
Dalotto-Moreno et al., "Targeting Galectin-1 Overcomes Breast Cancer-Associated Immunosuppression and Prevents Metastic Disease," Cancer Res. 73:1107-1117 (2013).
Juszczynski et al., "The AP1-dependent secretion of galactin-1 by Reed-Sternberg cells fosters immune privilege in classical Hodgkin lymphoma," Proc. Natl. Acad. Sci. USA 104:13134-13139 (2007).
Juszczynski et al., "MLL-Rearranged B Lymphoblastic Leukemias Selectively Express the Immunoregulatory Carbohydrate-Binding Protein Galectin-1," Clin. Cancer Res. 16:2122-2130 (2010).
Kamper et al., "Proteomic analysis identifies galectin-1 as a predictive biomarker for relapsed/refractory disease in classical Hodgkin lymphoma," Blood 117:6638-6649 (2011).

(Continued)

*Primary Examiner* — Mark Halvorson
(74) *Attorney, Agent, or Firm* — Foley Hoag LLP

(57) ABSTRACT

The present invention is based, in part, on the discovery of anti-galectm-1 (Gal 1.) monodonai antibodies useful for diagnostic and prognostic applications, as well as immunoglobulins, polypeptides, and nucleic acids thereof.

17 Claims, 13 Drawing Sheets

Specification includes a Sequence Listing.

(56) References Cited

OTHER PUBLICATIONS

Laderach et al., "A Unique Galectin Signature in Human Prostate Cancer Progression Suggests Galectin-1 as a Key Target for Treatment of Advanced Disease," Cancer Res. 73:86-96 (2013).

Le et al., "Galectin-1: A Link Between Tumor Hypoxia and Tumor Immune Privilege," J. Clin. Oncol. 23:8932-8941 (2005).

Lopez-Lucendo et al., "Growth-regulatory human galectin-1: crystallographic characterisation of the structural changes induced by single-site mutations and their impact on the thermodynamics of ligand binding," J. Mol. Biol. 343:957-970 (2004).

Mathieu et al., "Galectin-1 in Melanoma Biology and Related Neo-Angiogenesis Processes," J. Invest. Dermatol. 132:2245-2254 (2012).

Ouyang et al., "Viral induction and targeted inhibition of galectin-1 in EBV+posttransplant lymphoproliferative disorders," Blood 117:4315-4322 (2011).

Ouyang et al., "Galectin-1 serum levels reflect tumor burden and adverse clinical features in classical Hodgkin lymphoma," Blood 121:3431-3433 (2013).

Rodig et al., "AP1-Dependent Galectin-1 Expression Delineates Classical Hodgkin and Anaplastic Large Cell Lymphomas from Other Lymphoid Malignancies with Shared Molecular Features," Clin. Cancer Res. 14:3338-3344 (2008).

Rubinstein et al., "Targeted inhibition of galectin-1 gene expression in tumor cells results in heightened T cell-mediated rejection: A potential mechanism of tumor-immune privilege," Cancer Cell 5:241-251 (2004).

Tang et al., "Identification of Galectin-1 as a novel biomarker in nasopharyngeal carcinoma by proteomic analysis," Oncol. Reports 24:495-500 (2010).

Wu et al., "Overexpression of galectin-1 is associated with poor prognosis in human hepatocellular carcinoma following resection," J. Gastroenterol. Hepatol. 27:1312-1319 (2012).

International Search Report dated Feb. 11, 2015 from PCT/US2014/047783.

International Search Report dated Jan. 14, 2015 from PCT/US2014/047784.

Extended European Search Report dated Feb. 24, 2017 for EP Application No. 14828887.1, 7 pages.

Extended European Search Report dated Mar. 30, 2017 for EP Application No. 14829106.5, 8 pages.

GenBank Accession No. U05693-1. Mus spretus beta-galactoside-binding lectin gene, partial cds and 3' UTR. Feb. 4, 1995, p. 1.

Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," J Protein Chem, 11(5): 433-444 (1992).

Lederman et al., "A Single Amino Acid Substitution in a Common African Allele of the CD4 Molecule Ablates Binding of the Monoclonal Antibody, OKT4," Mol Immunol, 28(11): 1171-1178 (1991).

Li et al., "beta-Endorphin Omission Analogs: Dissociation of Immunoreactivity from Other Biological Activities," Proc Natl Acad Sci USA, 77(6): 3211-3214 (1980).

\* cited by examiner

ANTI-GALECTIN-1 MONOCLONAL ANTIBODIES AND FRAGMENTS THEREOF

BACKGROUND OF THE INVENTION

Galectin-1 (Gal1), a member of a conserved family of carbohydrate-binding proteins, modulates immune responses and fosters tumor-immune escape through specific recognition of N-acetyllactosamine (Gal-β1-4-NAcGlc) residues on the branches of N- or O-linked glycans (Juszczynski et al. (2007) *Proc Natl Acad Sci USA.* 104:13134-13139; Rabinovich and Croci (2012) *Immunity* 36:322-335; Rabinovich and Toscano (2009) *Nat. Rev Immunol,* 9:338-352; Rubinstein et al. (2004) *Cancer Cell* 5:241-251).

Gal1 selectively induces the apoptosis of cytotoxic T cells and T helper (Th) 1 and Th17 cells by interacting with specifically sialated cell surface glycoproteins, such as CD45, CD43 and CD7 (Toscano et al. (2007) *Nat. Immunol.* 8:825-834). Since Th2 cells and regulatory T (Treg) cells lack the Gal1-binding glycoprotein motif, Gal1 spares these cells and fosters an immunosuppressive Th2/Treg-enriched tumor microenvironment (Toscano et al. (2007) *Nat. Immunol.* 8:825-834). Gal1 also promotes the expansion of regulatory T (Treg) cells (Juszczynski et al. (2007) *Proc Natl Acad Sci USA.* 104:13134-13139; Toscano et al. (2007) *Nat. Immunol.,* 8:825-834) and Gal1-glycan interactions augment hypoxia-driven tumor angiogenesis (Croci et al. (2012). *J. Exp. Med.* 209; 1985-2000).

These molecular mechanisms underlie the effect of Gal1 on promoting classical Hodgkin lymphoma (cHL). cHL is a B-cell malignancy diagnosed in approximately 20,000 new patients in North America and Europe each year; >90% of these patients are young adults. cHL include small numbers of malignant Hodgkin Reed-Sternberg (HRS) cells within an extensive Th2/Treg-skewed inflammatory infiltrate (Küppers et al. (2002) *Ann. Oncol.* 13:11-18; Juszczynski et al. (2007) *Proc Natl Acad Sci U.S.A.* 104:13134-13139; Küppers (2009) *Nat. Rev. Cancer* 9:15-27). HRS cells overexpress Gal1, which selectively Th1 and cytotoxic T cells and promotes the immunosuppressive Th2/Treg-predominant HL microenvironment (Juszczynski et al. (2007) *Proc Natl Acad Sci USA.* 104:13134-13139). HRS cells lack B-cell receptor-mediated signals and rely on alternative survival and proliferative pathways activated by transcription factors, such as NF-κB and activator protein 1 (AP1) (Küppes et al. (2002) *Ann. Oncol.* 13:11-18; Mathas et al. (2002) *EMBO J.* 21:4104-4113; Schwering et al. (2003) *Mol. Med.* 9:85-95). In cHL, the tumor cells exhibit constitutive AP1 activation, express high levels of the AP1 components, cJun and Jun B, and depend on AP1-mediated proliferation signals (Mathas et al (2002) *EMBO J.* 21:4104-4113; Juszczynski al. (2007) *Proc Acad Sci USA.* 104:13134-13139; Rodig et al. (2008) *Clin. Cancer Res.* 14:3338-3344). Although primary cHLs have a brisk inflammatory infiltrate, there is little evidence of an effective host antitumor immune response. The reactive T cell population included predominantly Th2-type and CD4+CD25hiFoxP3+ regulatory T cells that directly suppress immune responses and protect HRS cells from immune attack (Re et al. (2005) *J. Clin. Oncol.* 23:6379-6386; Marshall et al. (2004) *Blood* 103:1755-1762; Gandhi et al. (2006) *Blood* 108:2280-2289). Th1 and natural killer and cytotoxic T cells are markedly underrepresented.

Increased Gal1 expression in immunohistochemical analyses of primary cHLs is associated with poorer event-free survival (Kamper et al. (2011) *Blood* 117:6638-6649). In particular; elevated serum Gal1 levels are significantly associated with tumor burden and adverse clinical features in newly diagnosed patients with cHL (Ouyang et al. (2013) *Blood* 121:3431-3433). Moreover, Gal1 expression is also associated with EBV-associated post-transplant lymphoproliferative disorder (PTLD) (Gottschalk et al. (2005). *Annu. Res. Mol.* 56:29-44; Ouyang et al. (2011) *Blood* 117:4165-4166 and 4315-4322), MLL-rearranged ALL (Juszczynski et al (2010) *Clin. Cancer Res.* 16:2122-2130), and Kaposi's sarcoma (Tang et al. (2010) *Oncol. Rep.* 24:495-500). In addition to these select lymphoid malignancies and virally induced cancers, Gal1 is also expressed by many solid tumors, including, breast cancer (Croci al, (2012) *J. Exp. Med.* 209:1985-2000), prostate cancer (Dalotto-Moreno et al. (2013) *Cancer Res.* 73:1107-1117), lung cancer (Laderach et al. (2013) *Cancer Res.* 73:86-96), pancreatic cancer (Chung et al. (2012) *Clin. Cancer Res.* 18:4037-4047), squamous cell carcinoma of the head and neck (Chung et al. (2008) *ANZ J. Surg.* 78:245-251; Alves et al. (2011) *Pathol. Res. Pract.* 207:236-40), hepatocellular carcinoma (Le et al. (2005) *J. Clin. Oncol.* 23:8932-41), nasopharyngeal carcinoma (Wu et al. (2012) *J. Gastroenterol. Hepatol.* 27; 1312-1319), and melanoma (Rubinstein et al. (2004) *Cancer Cell* 5:241-251; Mathieu et al. (2012) *J. Invest. Dermatol.* 132:2245-2254). Gal1 expression has been identified as an adverse prognostic marker in the above-mentioned solid tumors. Moreover, Gal1 silencing is associated with anti-tumor effects in breast cancer (Croci et al (2012). *J. Exp. Med.* 209:1985-2000), prostate cancer (Dalotto-Moreno et al. (2013) *Cancer Res.* 73:1107-1117), lung cancer (Laderach et al. (2013) *Cancer Res.* 73:86-96), and melanoma (Rubinstein et al. (2004) *Cancer Cell* 5:241-251).

Given the broadly immunosuppressive activities of Gal1, these results suggest that Gal1 is a very powerful diagnostic marker that may potentially guide the targeted, rational therapy in many cancers. Although potent therapeutic (i.e., neutralizing) Gal1 monoclonal antibodies that protect Th1 and cytotoxic T cells from Gal1-induced apoptosis (Ouyang al, (2011) *Blood* 117:4315-4322); abrogate Gal1-associated tumor angiogenesis (Croci et al. (2012). *J. Exp. Med.* 209:1985-2000), and limit the growth of Gal1$^+$ tumors in vivo (Croci et al. (2012) *J. Exp. Med.* 209:1985-2000) are known, such reagents may not be optimal for diagnostic and prognostic purposes.

In view of the above, it is clear that there remains a need in the art for compositions and methods to specifically detect Gal1, particularly in minimally invasive scenarios such as in serum-based assays.

SUMMARY OF THE INVENTION

The present invention relates in general to anti-galectin-1 (Gal1) monoclonal antibodies, and immunoglobulins, polypeptides, and nucleic acids thereof, useful for the diagnosis, prognosis, and monitoring of disorders associated with aberrant Gal1 expression (e.g., cancer).

In one aspect, a monoclonal antibody, or antigen-binding fragment thereof, is provided, wherein the monoclonal antibody comprises: a) a heavy chain sequence with at least about identity to a heavy chain sequence selected from the group consisting of the sequences listed in Table 1 or b) a light chain sequence with at least about 95% identity to a light chain sequence selected from the group consisting of the sequences listed in Table 1.

In one embodiment, the monoclonal antibody, or antigen-binding fragment thereof, comprises: a) a heavy chain CDR sequence with at least about 95% identity to a heavy chain CDR sequence selected from the group consisting of the sequences listed in Table 1 or b) a light chain CDR sequence with at least about 95% identity to a light chain CDR sequence selected from the group consisting of the sequences listed in Table 1. In another embodiment, the monoclonal antibody, or antigen-binding fragment thereof, comprises: a) a heavy chain sequence selected from the group consisting of the sequences listed in Table 1; or b) a light chain sequence selected from the group consisting of the sequences listed in Table 1. In still another embodiment, the monoclonal antibody, or antigen-binding fragment thereof, comprises: a) a heavy chain CDR sequence selected from the group consisting, of the sequences listed in Table 1; or b) a light chain CDR sequence selected from the group consisting the sequences listed in Table 1. In yet another embodiment, the monoclonal antibody, or antigen-binding fragment thereof, is chimeric, humanized, composite, murine, or human. In another embodiment, the monoclonal antibody or antigen-binding fragment thereof, is detectably labeled, comprises an effector domain, comprises an Fc domain, and/or is selected from the group consisting of Fv, Fav, F(ab')2), Fab', dsFv, say, sc(Fv)2, and diabodies fragments. In still another embodiment, the monoclonal antibody, or antigen-binding fragment thereof inhibits the binding of commercial antibody to Gal1. In yet another embodiment, the monoclonal antibody, or antigen-binding fragment thereof, is obtainable from hybridoma 8A12.H9.H10 deposited tinder deposit accession number PTA-120449.

In another aspect, an immunoglobulin heavy and/or light chain of any monoclonal antibody, antigen-binding fragment thereof, or protein comprising a CDR described herein, is provided.

In still another aspect, an isolated nucleic acid molecule that hybridizes, under stringent conditions, with the complement of a nucleic, acid encoding a polypeptide selected from the group consisting of the sequences listed in Table 1, or a sequence with at least about 95% homology to a nucleic acid encoding a polypeptide selected from the group consisting of the sequences listed in Table 1, is provided.

In yet another aspect, a vector comprising such an isolated nucleic acid is provided.

In another aspect, a host cell which comprises such an isolated nucleic acid, comprises such a vector expresses a monoclonal antibody or antigen-binding fragment thereof described herein, or is accessible under deposit accession number PTA-120449, is provided.

In still another aspect, a device or kit comprising at least one monoclonal antibody or antigen-binding fragment thereof described herein is provided, wherein said device or kit optionally comprises a label to detect the at least one monoclonal antibody or antigen-binding fragment thereof, or a complex comprising the monoclonal antibody or antigen-binding fragment thereof.

In yet another aspect, a method of producing a monoclonal antibody, or antigen-binding fragment thereof, describe herein is provided, which method comprises the steps of: (i) culturing a transformed host cell which has been transformed by a nucleic acid comprising a sequence encoding the monoclonal antibody, or antigen-binding fragment thereof, under conditions suitable to allow expression of said antibody, or antigen-binding fragment thereof; and (ii) recovering the expressed antibody, or antigen-binding fragment thereof.

In another aspect, a method of detecting the presence or level of a Gal1 polypeptide is provided, wherein said method comprises obtaining a sample and detecting said polypeptide in a sample by use of at least one monoclonal antibody, or antigen-binding fragment thereof, described herein. In one embodiment, the at least one monoclonal antibody or antigen-binding fragment thereof forms a complex with a Gal1 polypeptide and the complex is detected in the form of an enzyme linked immunosorbent assay (ELISA), radioimmune assay (RIA), immunochemically, or using an intracellular flow assay.

In still another aspect, a method for monitoring the progression of a disorder associated with aberrant Gal1 expression in a subject is provided, wherein the method comprises: a) detecting in a subject sample at a first point in time the level of expression of Gal1 using at least one monoclonal antibody, or antigen-binding fragment thereof, described herein; b) repeating step a) at a subsequent point in time; and c) comparing the level of expression of said Gal1 detected in steps a) and b) to monitor the progression of the disorder in the subject. In one embodiment, the subject has undergone treatment to ameliorate the disorder between the first point in time and the subsequent point in time.

In yet another aspect, a method for predicting the clinical outcome of a subject afflicted with a disorder associated with aberrant Gal1 is provided, wherein the method comprises: a) determining the level of expression of Gal1 in a patient sample using at least one monoclonal antibody, or antigen-binding fragment thereof, described herein; b) determining the level of expression of Gal1 in a sample from a control subject having a good clinical outcome using at least one monoclonal antibody, or antigen-binding fragment thereof, described herein; and c) comparing the level of expression of Gal1 in the patient sample and in the sample from the control subject; wherein a significantly higher level of expression in the patient sample as compared to the expression level in the sample from the control subject is an indication that the patient has a poor clinical outcome.

In another aspect, a method of assessing the efficacy of a therapy for a disorder associated with aberrant Gal1 in a subject is provided, wherein the method comprises comparing: a) the level of expression of Gal1 using at least one monoclonal antibody, or antigen-binding fragment thereof described herein, in a first sample obtained from the subject prior to providing at least a portion of the therapy to the subject, and b) the level of expression of Gal1 in a second sample obtained from the subject following provision of the portion of the therapy, optionally using at least one monoclonal antibody, or antigen-binding fragment thereof, described herein, wherein significantly lower level of expression of Gal1 in the second sample relative to the first sample, is an indication that the therapy is efficacious for inhibiting the disorder in the subject.

In still another aspect, a method of assessing the efficacy of a test compound for inhibiting a disorder associated with aberrant Gal1 in a subject is provided, wherein the method comprises comparing: a) the level of expression of Gal1 using at least one monoclonal antibody, or antigen-binding, fragment thereof, described herein, in a first sample obtained from the subject and exposed to the test compound, and b) the level of expression of Gal1 in a second sample obtained from the subject, optionally using at least one monoclonal antibody, or antigen-binding fragment thereof described herein, wherein the second sample is not exposed to the test compound, and a significantly lower level of expression of Gal1, relative to the second sample, is an indication that the test compound is efficacious for inhibiting the disorder in the subject. In one embodiment, the first and second samples are portions of a single sample obtained from the subject or portions of pooled samples obtained from the subject.

In any method described herein, the disorder can be selected from the group consisting of classical Hodgkin lymphoma (cHL), anaplastic large cell lymphoma (ALCL), MLL-rearranged ALL, EBV-positive post-transplant lymphoproliferative disorder (PTLD), nasopharyngeal carcinoma, Kaposi's sarcoma, breast cancer, prostate cancer, lung cancer, pancreatic cancer, squamous cell carcinoma of the head and neck, hepatocellular carcinoma, melanoma, gastrointestinal cancer, thyroid papillary carcinoma, laryngeal squamous cell carcinoma, and cutaneous T-cell lymphoma. Similarly, in some embodiments, the sample comprises cells, serum, peritumoral tissue, and/or intratumoral tissue obtained from the subject. In other embodiments, a significant increase comprises an at least two fold increase between the level of expression of Gal1 in the subject sample relative to the normal level of expression of Gal1 in the sample from the control subject. In still other embodiments, the subject is a human.

BRIEF DESCRIPTION OF FIGURES

FIG. 4A shows Gal1 levels in cHL patients and normal healthy donors (93.0±56.5 ng/ml vs. 36.9±7.8 ng/ml, p<0.0001). FIG. 4B shows Gal1 levels in patients on the risk-adapted clinical trials, HD13 (early-stage low-risk), HD14 (early-stage with risk factors) or HD18 (bulky localized or advanced-stage disease). FIG. 4C shows Gal1 levels in cHL patients with Ann Arbor stage I, II, III or IV disease. Nominal p-values are presented.

FIG. 5A shows Western blot analysis of cell lysates derived from genetically characterized diffuse large B-cell lymphoma (DLBCL) lines (SU-DHL4. OCI-Ly1) and Hodgkin lymphoma cell lines (L428, SUP-HD1, HDLM2). Lysates were probed with a rabbit monoclonal antibody recognizing PD-L1 (top panel) showing a band at the expected size of the fully glycosylated form of PD-L1 (~55 kDa). The gene copy number (CN) for the CD274 (PD-L1) locus, 9p24.1, is shown, as reported previously, for each cell line. Equal loading was demonstrated by probing for GAPDH. IHC analysis of formalin-fixed, paraffin embedded (FFPE) Hodgkin cell line HDLM2 (FIG. 5B) and DLBCL cell line DHL4 (FIG. 5C) stained with the rabbit anti-PD-L1 antibody showing membranous staining of the HDLM2 cells but no staining, of DHL4 insets show similar staining patterns with the mouse monoclonal anti-PD-L1 antibody. FIG. 5D shows FFPE human tonsil stained with rabbit anti-PD-L1 antibody showing little staining of lymphoid cells and weak membranous staining of occasional macrophages (inset, arrow). FIG. 5E shows human placenta stained with the rabbit PD-L1 monoclonal antibody (original lot concentration of 0.22 mg/ml) and demonstrates membrane staining of syncytiotrophoblasts.

FIG. 6A shows a representative example nodular sclerosis classical Hodgkin lymphoma (NSCHL) stained with the rabbit anti-PD-L1 antibody showing distinct membranous staining of Reed-Sternberg (RS) cells and intratumoral macrophages. Inset shows staining with PD-L1 highlighting the cell membrane of RS cells (arrow) as well as non-malignant cells, and macrophages (arrowheads) double stained with PD-L1 and the macrophage marker CD68. FIG. 6B shows a representative case of nodular lymphocyte-predominant Hodgkin lymphoma (NLPHL) stained with rabbit anti-PD-L1 showing LP cells (arrows) that are negative for PD-L1. FIG. 6C shows a representative case of primary mediastinal large B-cell lymphoma (PMBCL) stained with rabbit anti-PD-L1 antibody showing predominantly membranous staining of lymphoma cells. FIG. 6D shows a representative case of EBV-positive Burkitt lymphoma (BL) stained with rabbit anti-PD-L1 antibody showing negative staining in either the tumor cells or the intermixed, tumor-associated macrophages.

DETAILED DESCRIPTION OF THE INVENTION

Figure 1:
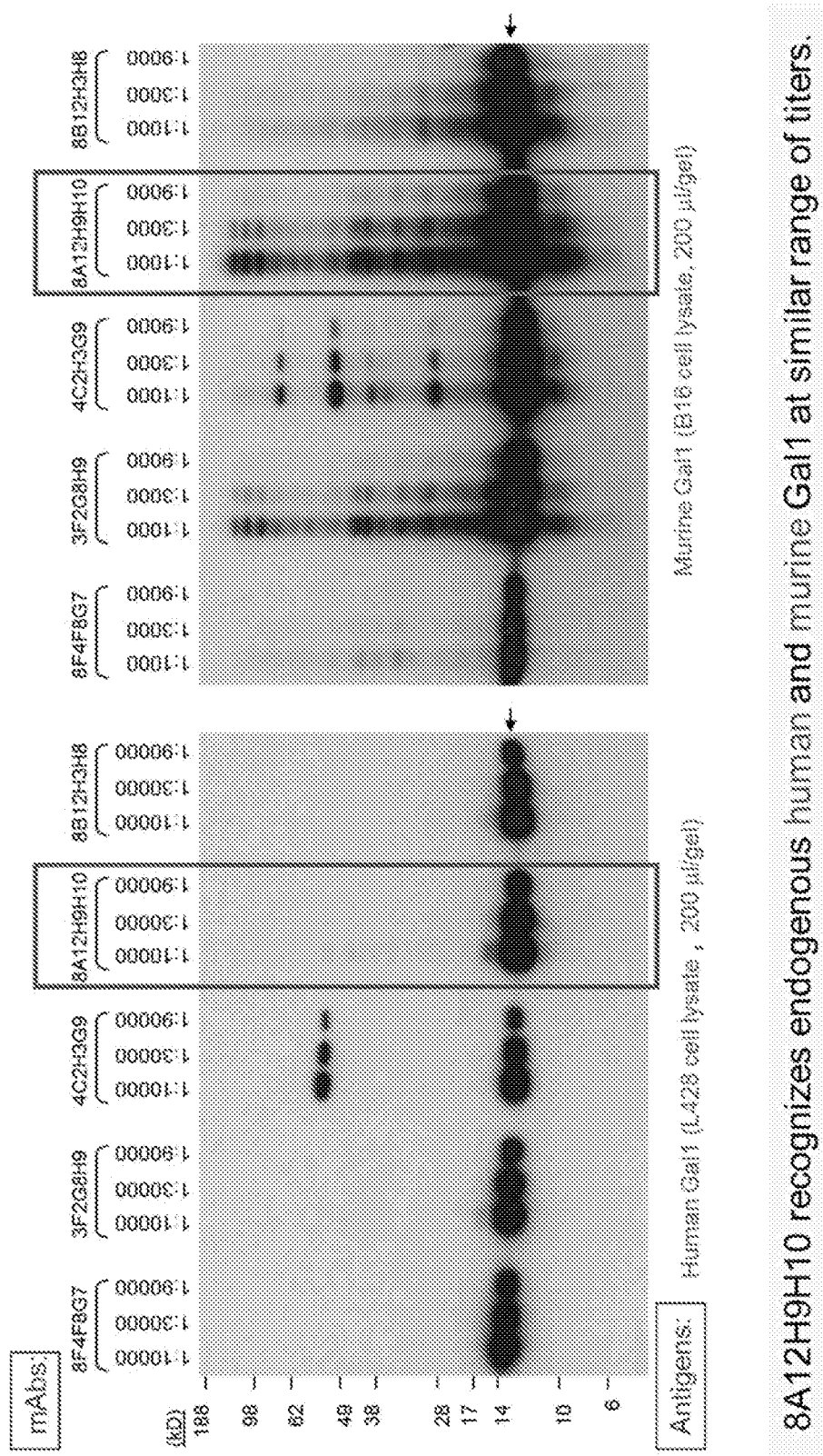
FIG. 1 shows cross-reactivity of anti-Gal1 monoclonal antibody, 8A12, on endogenous human and murine Gal1 on Western-blot (WB). WB analysis of cell lysates derived from human Hodgkin lymphoma line, L428 and murine melanoma line, B16-F10. Lysates were probed with 8A12 at different titration showing a specific band of Gal1 (~14 kDa), 8A12 recognizes endogenous human and murine Gal1 at similar range of titres.

The present invention is based in part on the discovery of new anti-Gal1 monoclonal antibodies that can bind to detect Galectin1 in at least an unexpectedly superior manner in m no detection assays (e.g., Western blot, immunohistochemistry, flow cytometry, and the like) and without neutralizing its function. Such antibodies are particularly useful for the multiplex (e.g., combinatorial) detection of Gal1 and other immunoinhibitory molecules, such as PD-1, PD-L1, PD-L2, CTLA4, and the like.

I. Definitions

The articles "a" and "an" are used herein to refer to one or to more than one (i.e. to at least one) of the grammatical object of the article. By way of example, "an element" means one element or more than one element.

The term "altered amount" of a marker of a marker refers to increased or decreased copy number of a marker and/or increased or decreased nucleic acid level of a particular marker gene or genes in a sample, as compared to that of the marker in a control sample. The term "altered amount" of a marker also includes an increased or decreased protein level of a marker in a sample, as compared to the protein level of the marker in a normal, control sample.

The term "altered activity" of a marker refers to an activity of a marker which is increased or decreased in a disease state, e.g., in a biological sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker; or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides or, for example, through cellular analyses such as internalization of normally extracellular mature functional Gal1.

The term "angiogenesis" or "neovascularization" refers to the process by which new blood vessels develop from pre-existing vessels (Varner et al. 1999) *Angiogen.* 3:53-60; Mousa et al. (2000) *Angiogen. Stim. Inhib.* 35:42-44. Kim et al. (2000) *Amer. J. Path.* 156:1345-1362; Kim et al. (2000) *J. Biol. Chem.* 275; 33920-33928; Kumar at al. (2000) Angiogenesis: From Molecular to Integrative Pharm. 169-180). Endothelial cells from pre-existing blood vessels or from circulating endothelial stem cells (Takahashi et al. (1995) *Nat. Med.* 5:434-438; Isner et al. (1999). *J. Clin. Invent.* 103:1231-1236) become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

For example, the term "tissue exhibiting angiogenesis" refers to a tissue in which new blood vessels are developing from pre-existing blood vessels.

As used herein, the term "inhibiting angiogenesis" "diminishing angiogenesis," "reducing angiogenesis," and grammatical equivalents thereof refer to reducing the level of angiogenesis in a tissue to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control tissue, and most preferably is at the same level which is observed in a control tissue. A reduced level of angiogenesis need not, although it may, mean an absolute absence of angiogenesis. The invention does not require, and is not limited to, methods that wholly eliminate angiogenesis. The level of angiogenesis may be determined using methods well known hi the art, including, without limitation, counting the number of blood vessels and/or the number of blood vessel branch points, as discussed herein and in the examples. An alternative in vitro assay contemplated includes the tubular cord formation assay that shows growth of new blood vessels at the cellular level [D. S. Grant et al., *Cell*, 58: 933-943 (1989)]. Art-accepted in vivo assays are also known, and involve the use of various test animals such as chickens, rats, mice, rabbits and the like. These in vivo assays include the chicken chorioallantoic membrane (CAM) assay, which is suitable for showing, anti-angiogenic activity in both normal and neoplastic tissues (Ausprunk (1975) *Amer. J. Path.* 79:597-610 and Ossonowski and Reich (1980) *Cancer Res.* 30:2300-2309). Other in vivo assays include the mouse metastasis assay, which shows the ability of a compound to reduce the rate of growth of transplanted tumors in certain mice, or to inhibit the formation of tumors or preneoplastic cells in mice which are predisposed to cancer or which express chemically-induced cancer (Humphries al. (1986) *Science* 233:467-470 and Humphries et al. (1988) *J. Clin. Invest* 81:782-790). Moreover, in some embodiments, angiogenesis can be measured according to such attributes as pericyte maturation and vascular remodeling as described further herein.

As used herein, the term "hypoxia associated angiogenesis" "hypoxia-induced angiogenesis" refers generally to the process of pathological angiogenesis in non-neoplastic disease states and is typically, although not necessarily, accompanied by a transition to a neoplastic state. Hypoxia-induced transcription factors (HIFs) induce the expression of angiogenic factors including HIF-1zlpha, VEGF, nitric oxide synthase, PDFG, Ang2, and others. As a result, hypoxia associated angiogenesis encompasses a well-known set of pathological conditions characterized by such a process Pugh et al. (2003) *Nat. Med* 9, 677-684; Fraisl et al. (2009) *Dev Cell* 16, 167-179; Ferrara et al. (2005) *Nature* 438, 967-974; Ferrara, N, (2010) *Cytokine Growth Factor Rev* 21, 21-26], in some embodiments, the set of hypoxia associate angiogenesis pathologies includes, but is not limited to, neoplasms and cancers, age-related macular degeneration, diabetes retinopathy, atherosclerosis, chronic obstructive lung disease, and psoriasis.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., Gal1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA genomic sequences, in order to generate expression vectors encoding, complete IgG polypeptides or other isotypes. VH and VL can also be used in the generation of Fab, FV or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. USA* 90; 6444-6448; Poljak, R., J, et al. (1994), *Structure* 2:1121.-1123).

Still further, an antibody or antigen-binding portion thereof may be part of larger immunoadhesion polypeptides, formed by covalent or noncovalent association of the antibody or antibody portion with one or more other proteins or peptides. Examples or such immunoadhesion polypeptides include use of the streptavidin core region to make a tetrameric scFv, polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., al. (1994) *Mol. Immumol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In one embodiment, antibodies of the present invention hind specifically or substantially specifically to Gal1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted of secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of immunological Interest," $5^{th}$ Edition, U.S. Department of Health and Human Services, 1992: Chothia et al. (1987) J. Mol. Biol. 196, 901; and MacCallum et al., J. Mol. Biol. (1996) 262, 732, each of which is incorporated by reference in its entirety).

As used herein, the term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is skin to differentiating the disease state of the sample from another disease state.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable abase pairing with nucleotide residues in the second portion. In another embodiment, all nucleotide residues of the first portion axe capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germane immunoglobulin sequences and variable regions comprising human germline or non-germline sequences from two or more unrelated human variable regions.

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B), IgG3 and IgG4.

As used herein, "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including, allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g., standard saline citrate, pH 7.4) without a substantial fraction of the molecule dissociating from the substrate.

As used herein, "Framework" or "FR" residues are those variable-domain residues other than the HVR residues as herein defined.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "heterologous antibody" is defined relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50'N homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions an occupied by the same nucleotide residue.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell hut to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering, the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are frictional and stable in the absence of light chain (see, e.g.; Hamers-Casterman et al. (1993) Nature 363:446-448 (1993) and Sheriff et al., (1996) Nature Struct. Biol. 3, 733-736).

As used herein, the term "immune cell" refers to cells that play a role in the immune response. Immune cells are of hematopoietic origin, and include lymphocytes, such as B cells and T cells; natural killer cells; myeloid cells, such as monocytes, macroghages, eosinophils, mast cells, basophils, and granulocytes.

As used herein, the term "immune disorder" includes immune diseases, conditions, and predispositions to, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, or MLL® pre B-cell ALL), cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies) eosinophilia, conjunctivitis, glomerular nephritis systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibit" includes the decrease, limitation, or blockage, of, for example a particular action, function, or interaction.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

As used herein, the term an "isolated antibody" is intended to an to an antibody which is substantially free of other antibodies having different antigenic specificities (e.g., an isolated antibody that specifically binds to human Gal1 and is substantially free of antibodies that do not bind to Gal1). An isolated antibody that specifically binds to an epitope of human Gal1 may, however, have cross-reactivity to other Gal1 proteins, respectively, from different species. However, in some embodiments, the antibody maintains higher affinity and selectivity for human Gal1. In addition, an isolated antibody is typically substantially free of other cellular material and/or chemicals. In one embodiment of the present invention, a combination of "isolated" monoclonal antibodies having different specificities to human Gal1 are combined in a well defined composition.

As used herein, an "isolated protein" refers to a protein that is substantially free of other proteins, cellular material, separation medium and culture medium when isolated from cells or produced by recombinant DNA techniques, or Chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a target polypeptide (e.g., immunoglobulin) or fragment thereof, in which the protein is separated from cellular components of the cells from which it is isolated or recombinantly produced. In one embodiment, the language "substantially free of cellular material" includes preparations of target protein or fragment thereof, having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When antibody, polypeptide, peptide or fusion protein or fragment thereof, e.g., a biologically active fragment thereof, is recombinantly produced, it is also preferably substantially free of culture medium. i.e., culture medium represents less than about 20%, more preferably less than about 10%, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent; e.g., a probe, tot specifically detecting or modulating the expression of a marker of the present invention. The kit may be promoted, distributed, or sold as a unit for performing the methods of the present invention.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having genome comprising a human heavy chain transgene and a light chain transgene fused to an immortalized cell.

A "post-transplantation lymphoproliferative disorder", "PTLD", and/or "viral-associated PTLD" each refers to a disorder in which lymphocytes, which are white blood cells produced in the lymphatic tissue (e.g., lymph nodes, spleen, and/or thymus), are over-produced or act abnormally and are caused by or correlated with a virus. Lymphoid cells include thymus derived lymphocytes (T cells); bone marrow-derive lymphocytes (B cells), and natural killer (NK cells), for example. Lymphocytes progress through a number of different stages, including proliferation, activation, and maturation, and lymphoma or aberrant proliferation can develop at each stage. Disorders may be malignant neoplasms (and may be classified as aggressive or indolent, or as low, intermediate or high-grade), including those associated with IFN-gamma., or the disorders may involve non-malignant aberrant expansion of lymphoid cells. LPDs include any monoclonal or polyclonal LPD that is not resolving without treatment and/or that involves excessive cellular proliferation, such as an expanding, monoclonal, polyclonal or oligoclonal, lymphoid neoplasm. Cellular proliferation may be more rapid than normal and may continue after the stimuli that initiated the new growth cease. A neoplasm will show partial or complete lack of structural organization and functional coordination with the normal tissue, and may form a distinct mass of tissue that may be either benign (benign tumor) or malignant (cancer).

Such viral-associated PTLD may be caused by or associated with, e.g., Epstein-Barr virus (EBV), a herpes virus, HHV-8, cytomegalovirus, C-type retrovirus, human T-lymphotropic virus type 1 (C-type retrovirus), and/or human immunodeficiency virus (HIV, HIV-1, HIV-2). HIV- and/or AIDS-associated cancers include HIV-associated LPDs, such Karposi sarcoma, non-Hodgkin's lymphoma, central nervous system (CNS) lymphoma, adult T-cell leukemia/lymphoma (HTLV-1+), and AIDS-associated lymphoma. Immune deficiency such as in AIDS patients, organ transplant recipients, and genetic immune disorders may allow latent EBV to reactivate, causing proliferation of abnormal lymphocytes and the potential to develop an EBV-associated LPD, for example. Methods to detect the presence of virus or viral infection in an aberrant cell, such as a cell involved in a PTLD, are known in the art. Viral nucleic; acids or polypeptides may be detected in a cell, tissue, or organism such as an aberrant cell, for example. Also, methods to detect immune response specific for a virus are known. A delayed type-hypersensitivity (DTH) assay, such as a trans vivo DTH assay may be used to detect regulatory T cells, for example. In such an assay, human or other mammalian peripheral blood mononuclear cells (PBMC) may be mixed with a carrier control with and without viral antigen, for example, and injected into a heterologous naive recipient, such as the pinnae or footpad of naive mice. If the donor of the PBMC had previously been sensitized to the challenge antigen, DTH-like swelling responses are observed.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the present invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the present invention. A marker protein comprises the entire or a partial sequence of any of the sequences set forth in the Sequence Listing. The terms "protein" and "polypeptide" are used interchangeably.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a viral-associated PTLD. An "over-expression" or "significantly higher level of expression" of a marker refers to an expression level in a test sample that is greater than the standard error of the assay employed to assess expression, and is preferably at least twice and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., $V_H$, $V_L$, CDR3) that bind to Gal1, is intended to refer to a nucleic acid molecule in which the nucleotide sequences encoding the antibody or antibody portion are free of other nucleotide sequences encoding antibodies or antibody portions that bind antigens other than Gal1, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 7.1, 7.7, 7.3, 7.4, 7.5, 7.6, 7.7, 7.8, 7.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/monamer homology element.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention "response" is generally related to for example, determining, the effects on progression efficacy, or outcome of a clinical intervention. In some embodiments, responses relate directly to a change in tumor mass and/or volume after initiation of clinical intervention (e.g., administration of an anti-Gal1 monoclonal antibody). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR). "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-19}$ M or even lower when determined by surface plasmon resonance (SPR) technology in a BIACORE® assay instrument using human Gal1 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, "subject" refers to any healthy animal, mammal or human, or any animal, mammal or human afflicted with a viral-associated PTLD, e.g., EBV-associated PTLD. The term "subject" is interchangeable with "patient". The term "non-human animal" includes vertebrates, e.g., mammals and non-mammals, such as non-human primates, sheep, dog, cow, chickens, amphibians, reptiles, etc.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following, survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcripts" is a polynucleotide. (e.g. an mRNA, hnRNA, a cDNA, or an analog, of such RNA or cDNA) which is complementary to or homologous with all or a portion of a mature mRNA made by transcription of a marker of the present invention and normal post-transcriptional processing (e.g., splicing), if any, of the RNA transcript, and reverse transcription of the RNA transcript.

As used herein, the term "T cell" includes CD4+ T cells and CD8+ T cells. The term T cell also includes both helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "unrearranged" or "germline configuration" in reference to a V segment refers to the configuration wherein the V segment is not recombined so as to be immediately adjacent to a D or J segment.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

For nucleic acids, the term "substantial homology" indicates that two nucleic acids, or designated sequences thereof, when optimally aligned and compared, are identical, with appropriate nucleotide insertions Or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 20, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix and a gap weight of 16, 14, 12, 10, 8, 6, or 4 and a length weight: of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score-100, wordlength-12 to obtain nucleotide sequences homologous to the nucleic acid molecules of the present invention. BLAST protein searches can be performed with the XBLAST program, score=50, word-length=3 to obtain amino acid sequences homologous to the protein molecules of the present invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web al the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (see, F. Ausubel, et al., ed. Current Protocols in Molecular Biology, Greene Publishing and Wiley Interscience, New York (1987)).

II. Monoclonal Antibodies, Immunoglobulins, and Polypeptides

The present invention relates, in part, to isolated monoclonal antibodies or fragments thereof that are directed against Gal1. Such molecules are characterized in that they exhibit a superior ability to recognize Gal1 protein in diagnostic assays, such as immunohistochemical (IHC), Western blot, intercellular flow, ELISA, and the like, compared to known anti-Gal1 antibodies or those that neutralize Gal1 protein function.

Sequences, structures, domains, biophysical characteristics, and functions of Gal1 gene and gene products have been described in the art. See, for example, Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004) *Curr Opin Struct Biol* 14:617-630, Toscano et al. (2007) *Cyt Growth Fact Rev* 18:57-71; Camby et a., (2006) *Glycobiol* 16:137R-157R; U.S. Pat. Publs. 2003-0004132, 2003-0109454, 2006-0189514, 2009-0176223, 2009-0191182, 2012-0028825, and 2013-0011409, each of which is incorporated herein, by reference, in its entirety. The nucleic acid and amino acid sequences of a representative human Gal1 biomarker is available to the public at the GenBank database under NM_0023053 and NP_002296.1. Nucleic acid and polypeptide sequences of Gal1 orthologs in organisms other than humans are well known and include, for example, monkey Gal1 (NM_001168627.1 and NP_001162098.1), chimpanzee Gal1 (XM_003953882.1 and XP_003953931.1; XM_003953883.1 and XP_003953932.1; XM_001162104.3 and XP_001162104.1), mouse Gal1 (NM_008495.1 and NP_032521.1), rat Gal1 (NM_019904.1 and NP_063969.1), dog Gal1 (NM_001201488.1 and NP_00188417.1), chicken Gal1 (NM_206905.1 and NP_99678.1), and cow Gal1 (NM_175782.1 and NP_786976.1). For example, relevant Gal1 sequences useful for detection include those listed below:

Human Gal1 cDNA Sequence

SEQ ID NO: 1

1 atggcttgtg gtctggtcgc cagcaacctg aatctcaaac ctggagagtg ccttc-gagtg

```
 61 cgaggcgagg tggctcctga cgctaagagc ttcgtgctga acctgggcaa agacag-
    caac 121 aacctgtgcc tgcacttcaa ccctcgcttc aacgcccacg gcgacgccaa cac-
    catcgtg 181 tgcaacagca aggacggcgg ggcctggggg accgagcagc gggaggctgt ctttc-
    ccttc 241 cagcctggaa gtgttgcaga ggtgtgcatc accttcgacc aggccaacct gaccgt-
    caag 301 ctgccagatg gatacgaatt caagttcccc aaccgcctca acctggaggc catcaac-
    tac 361 atggcagctg acggtgactt caagatcaaa tgtgtggcct ttgactga
```

15

Human Gal1 Amino Acid Sequence

```
                                                       SEQ ID NO: 2
  1 macglvasnl nlkpgeclrv rgevapdaks fvlnlgkdsn nlclhfnprf nahgdan-
    tiv 61 cnskdggawg teqreavfpf qpgsvaevci tfdqanltvk lpdgyefkfp nrln-
    leainy 121 maadgdfkik cvafd
```

Mouse Gal1 cDNA Sequence

```
                                                       SEQ ID NO: 3
  1 atggcctgtg gtctggtcgc cagcaacctg aatctcaaac ctggggaatg tct-
    caaagtt 61 cggggagagg tggcctcgga cgccaagagc tttgtgctga acctgggaaa agacag-
    caac 121 aacctgtgcc tacacttcaa tcctcgcttc aatgcccatg gagacgccaa caccatt-
    gtg 181 tgtaacacca aggaagatgg gacctgggga accgaacacc gggaacctgc cttc-
    cccttc 241 cagcccggga gcatcacaga ggtgtgcatc accttttgacc aggctgacct gaccat-
    caag 301 ctgccagacg gacatgaatt caagttcccc aaccgcctca acatggaggc catcaac-
    tac 361 atggcggcgg atggagactt caagattaag tgcgtggcct ttgagtga
```

45

Mouse Gal1 Amino Acid Sequence

```
                                                       SEQ ID NO: 4
  1 macglvasnl nlkpgeclkv rgevasdaks fvlnlgkdsn nlclhfnprf nahgdan-
    tiv 61 cntkedgtwg tehrepafpf qpgsitevci tfdqadltik lpdghefkfp nrln-
    meainy 121 maadgdfkik cvafe
```

Isolated monoclonal antibodies or fragments thereof that are directed against Gal1 are provided. In particular, the inventors have deposited the mAb 8A12.H9.H10 (i.e., the 8A12 antibody) producing hybridoma at the American Type Culture Collection (ATCC, 10801 University Boulevard, Manassas, Va. 20110 USA), in accordance with the terms of Budapest Treaty, on Jul. 2, 2013, under deposit number PTA-120449.

The variable domain of the light and heavy chains of the 8A12 mAb have been sequenced and the complementarity determining regions (CDRs) domains thereof are provided herein and in Table 1. For example, the 8A12 light chain variable (vK) polypeptide sequence is (SEQ ID NO: 5)
MMSPAQFLFLLVLWIQKTNGDVVMTQTPLTLSVTIGQPASISC<u>KSSQSLL</u>

<u>DSDGKTYLN</u>WLLQRPGQSPKRLIY<u>LLSKLDS</u>GVPDRFTGSGSGTDFTLQI

SRVEAEDLGFYYC<u>WQGTHFPYT</u>FGGGTKLEIK, wherein CDR definitions and protein sequence numbering are listed according to Kabat nomenclature and CDR amino acid sequences are underlined in order of CDR1, CDR2, and CDR3, respectively. Thus, the light chain variable CDR 1 (CDR-L1) is KSSQSLLDSDGKTYLN (SEQ ID NO: 12), CDR-L2 is LLSKLDS (SEQ ID NO: 15), and CDR-L3 is WQGTHFPYT (SEQ ID NO: 18). The 8A12 light chain variable (vK) polypeptide sequence is encoded by the following nucleic acid sequence (SEQ ID NO: 6):

```
  1 atgatgagtc ctgcccagtt cctgtttctg ttagtgctct ggattcagaa aac-
    caacggt 61 gatgttgtga tgactcagac cccactcact ttgtcggtta ccattggaca accagc-
    ctcc 121 atctcttgca agtcaagtca gagcctctta gatagtgatg gaaagacata tttgaat-
    tgg 181 ttgttacaga ggccaggcca gtctccaaag cgcctaatct atctgctgtc taaactg-
    gac 241 tctggagtcc ctgacaggtt cactggcagt ggatcaggga cagatttcac actg-
    caaatc 361 tacacgttcg gagggggac caagctggaa ataaaa
```

Similarly, the 8A12 heavy chain variable (vH) polypeptide sequence is MGWSGIFLFLLSVTTGVHSQAYLQQS-GAELVRPGASVRMSCKASGYTFT<u>RYNMH</u>WVKQT PRQGLEWIG <u>RIYPGNGDTSYNQKFKG</u>KATLTVDKSSSTAYMQLSS LTSEDSAVYFCTV<u>WDY</u>WGQGTTLTVSS (SEQ ID NO: 7), wherein, CDR definitions and protein sequence numbering are listed according to Kabat nomenclature and CDR amino acid sequences are underlined in order of CDR1, CDR2, and CDR3, respectively. Thus, CDR-H1 is RYNMH (SEQ ID NO: 23), CDR-H2 is RIYPGNGDTSYNQKFKG (SEQ ID NO: 26), and CDR-H3 is amino acids 118-120 of SEQ ID NO: 7. The 8A12 heavy chain variable (vH) polypeptide sequence is encoded by the following nucleic acid sequence (SEQ ID NO: 8):

```
  1 atgggatgga gcgggatctt tctcttcctc ctgtcagtaa ctacaggtgt ccactc-
    ccag 61 gcttatctac agcagtctgg ggctgagctg gtgaggcctg gggcctcagt gaggat-
    gtcc 121 tgcaaggctt ctggctacac tttcaccagg tacaatatgc actgggtaaa gcaga-
    cacct 181 agacagggcc tggaatggat tggacgtatt tatccaggaa atggtgatac ttccta-
    caat 241 cagaagttca agggcaaggc cacactgact gtagacaaat cctccagcac agccta-
    catg 301 cagctcagca gcctgacatc tgaagactct gcggtctatt tctgtacagt ctgggac-
    tac 361 tggggccaag gcaccactct cacagtctcc tca
```

Since it is well known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the present invention (e.g., including the sequences of Table 1, or portions thereof). The antibodies further can comprise the CDR2s of variable regions of the present invention (e.g., including the sequences of Table 1, or portions thereof). The antibodies further can comprise the CDR1s of variable regions of the present invention (e.g., including the sequences of Table 1, or portions thereof). In other embodiments, the antibodies can comprise any combinations of the CDRs.

The CDR1, 2, and/or 3 regions of the engineered antibodies described above can comprise the exact amino acid sequence(s) as those of variables regions of the present invention (e.g., including the sequences of Table 1, or portions thereof) disclosed herein. However, the ordinarily skilled artisan will appreciate that some deviation from the exact CDR sequences may be possible while still retaining the ability of the antibody to bind Gal1 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 1, or portions thereof).

The structural features of known, non-human or human antibodies (e.g., a mouse anti-human Gal1 antibody) can be used to create structurally related human anti-human Gal1 antibodies that retain at least one functional property of the antibodies of the present invention, such as binding to Gal1. Another functional property includes inhibiting binding of the original known, non-human or human antibodies in a competition ELISA assay.

In some embodiments, monoclonal antibodies capable of binding human Gal1 are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1.

Similarly, monoclonal antibodies capable of binding human Gal1, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

Monoclonal antibodies capable of binding human Gal1, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1 and comprising a light chain wherein the variable domain comprises at least a CDR having a sequence that is at least 80%, 85%, 90%, 91%, 92%, 93%. 94%, 95%, 96%, 97%, 98%, 99%, 99.5% or 100% identical from the group of light chain variable domain CDRs presented in Table 1, are also provided.

A skilled, artisan will, note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented in Table 1 and a light chain, wherein the variable domain comprises at least a CDR having a sequence selected from the group consisting of the light chain variable domain CDRs presented in Table 1.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding human Gal1 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth in Table 1 and/or the light chain variable domain of the monoclonal antibodies of the present invention can comprise or consist of the vκ amino acid sequence set forth in Table 1.

The monoclonal antibodies of the present invention can be produced and modified by any technique well known in the art. For example, such monoclonal antibodies can be murine antibodies, such as those obtainable from the hybridoma deposited on Jul. 2, 2013 with the ATCC as deposit PTA-120449. Similarly, such monoclonal antibodies can be chimeric, preferably chimeric mouse/human antibodies. In some embodiments, the monoclonal antibodies are humanized antibodies such that the variable domain comprises human acceptor frameworks regions, and optionally human constant domain where present, and non-human donor CDRs, such as mouse CDRs as defined above.

The present invention further provides fragments of said monoclonal antibodies which include, but are not limited to, Fv, Fab, F(ab')2, Fab', dsFv, scFv, sc(Fv)2 and diabodies: and multispecific antibodies formed from antibody fragments. For example, a number of immunoinhibitory molecules, such as Gal1, PD-L1, PD-L2, PD-1, CTLA-4, and the like, can be detected in a bispecific or multispecific manner in order to efficiently characterize the expression of such molecules.

Other fragments of the monoclonal antibodies of the present invention are also contemplated. For example, individual immunoglobulin heavy and/or light chains are provided, wherein the variable domains thereof comprise at least a CDR presented in Table 1. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented in Table 1. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein (e.g., presented in Table 1), are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1 CDR-L2, and CDR-L3.

In other embodiments, an immunoglobulin heavy and/or light chain according to the present invention comprises or consists of a vH or vκ variable domain sequence, respectively, provided in Table 1.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be use in an isolated (e.g., purified) form or contained in a vector, such as a membrane or lipid vesicle (e.g. a liposome).

III. Nucleic Acids, Vectors, and Recombinant Host Cells

A further object of the invention relates to a nucleic acid sequence encoding monoclonal antibodies and fragments thereof, immunoglobulins, and polypeptides of the present invention.

In a particular embodiment, the invention relates to a nucleic acid sequence encoding the vH domain of mAb 8A12 or the vL domain of mAb 8A12.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Thus, a further object of the invention relates to a vector comprising a nucleic acid of the present invention.

Such vectors may comprise regulatory elements, such as a promoter, enhancer, terminator and the like; to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Clinics S D et al. 1983) of immunoglobulin H chain and the like.

Any expression vector for animal cell can be used. Examples of suitable vectors include pAGE107 (Miyaji H. et al. 1990); pAGE103 (Mizukami T et al. 1987), pHSG274 (Brady G et al. 1984), pKCR (O'Hare K et al. 1981), pSG1 beta d2-4-(Miyaji H et al. 1990) and the like. Other representative examples of plasmids include replicating plasmids comprising an origin of replication, or integrative plasmids, such as for instance pUC, pcDNA, pBR, and the like. Representative examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cell. PsiCRIP cells, GPenv-positive cells, 293 cells, etc. Detailed protocols for producing such replication-defective recombinant viruses may be found for instance in WO 95/14785, WO 96/22378, U.S. Pat. Nos. 5,882,877, 6,013,516, 4,861, 719, 5,278,056 and WO 94/19478.

A further object or the present invention relates to a cell which has been transfected, infected or transformed by a nucleic acid and/or vector according to the invention. The term "transformation" means the introduction of a "foreign" (i.e. extrinsic or extracellular) gene, DNA or RNA sequence to a host cell, so that the host cell will express the introduced acne or sequence to produce a desired substance, typically a protein or enzyme coded by the introduced gene or sequence. A host cell that receives and expresses introduced DNA or RNA has been "transformed."

The nucleic acids of the present invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation; prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocyles, etc.). Examples also include mouse SP2/0-Ag14 cell (ATCC CRL1581), mouse P3X63-Ag8.653 cell (ATCC CRL 1580), CHO cell in which a dihydrofolate reductase gene (hereinafter referred to as "DHFR gene") is defective (Urlaub G et al: 1980), rat YB2/3/HL.P2.G11.16Ag.20 cell (ATCC CRL 1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody or a polypeptide of the invention according to the invention, said method comprising the steps consisting of (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody or polypeptide. Such recombinant host cells can be used for the production of antibodies and polypeptides of the invention.

In another aspect, the present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library. Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences. Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

IV. Methods of Producing Antibodies

Antibodies and fragments thereof, immunoglobulins, and polypeptides of the present invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies and other polypeptides of the present invention can be synthesized by recombinant DNA techniques as is wed-known in the art. For example, these fragments can be obtained as DNA expression products after incorporation of DNA sequences encoding the desired (polypeptide into expression vectors and introduction of such vectors into suitable eukaryotic or prokaryotic hosts that will express the desired polypeptide, from which they can be later isolated using well-known techniques.

In particular, the present invention further relates to a method of producing an antibody or a polypeptide of the invention, which method comprises the steps consisting of: (i) culturing a transformed host cell according to the invention under conditions suitable to allow expression of said antibody or polypeptide; and ii) recovering the expressed antibody or polypeptide.

Antibodies and other polypeptides of the present invention are suitably separated from the culture medium by conventional immunoglobulin purification procedures such as, for example, protein A-Sepharose, hydroxylapatite chromatography, gel electrophoresis, dialysis, affinity chromatography, ammonium sulfate or ethanol precipitation, acid extraction, anion or cation exchange chromatography, phosphocellulose chromatography, hydrophobic interaction chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Chimeric antibodies (e.g., mouse-human chimeras) of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. The CH domain of a human chimeric antibody can be any region which belongs to human immunoglobulin, such as the IgG class or a subclass thereof, such as IgG1, IgG2, IgG3 and IgG4. Similarly, the CL of a human chimeric antibody can be any region which belongs to Ig, such as the kappa class or lambda class. chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi; M. European Patent Application 171,496; Morrison et al. European Patent Application 173,494; Neuberger et al. PCT Application WO 86/01533; Cabilly et al. U.S. Pat. No. 4,816,567: Cabilly et al. European Patent Application 125,023; Better et al. (1988) *Science* 240:1041-1043: Lin et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84; 214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhocyan al. (1988) *Science* 239: 1534; and Beidler et al. (188) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. No. 5,565,332, 5,871,907, or 5,733,743. Humanized antibodies of the present invention can be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gone encoding an antibody heavy chain and a gene encoding an antibody light chain exists on separate vectors or of a type in which both genes exist on the same vector (tandem type).

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example; CDR-grafting (EP 239,400; PCT publication WO91/09967; U.S. Pat. Nos. 5,225,539; 5,530, 101; and 5,585,089), veneering or resurfacing (EP 592,106; EP 519,596; Padian E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Similarly, bispecific or multispecific antibodies described herein can be made according to standard procedures. For example, triomas and hybrid hybridomas are two examples of cell lines that can secrete bispecific or multispecific antibodies. Examples of bispecific and multispecific antibodies produced by a hybrid hybridoma or a trioma are disclosed in U.S. Pat. No. 4,474,893. Such antibodies can also be constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA*, 83:1453, and Staerz and Bevan (1986) *Immunol. Today* 7:241). Alternatively, such antibodies can also be generated by making heterohybridomas by fusing hybridomas or other cells making different antibodies, followed by identification of clones producing and co-assembling the desired antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more immunoinhibitory biomarkers described herein.

In addition, Methods for producing antibody fragments are well known. For example. Fab fragments of the present invention can be obtained by treating an antibody which specifically reacts with human GAL1 with a protease, papaine. Also, Fabs can be produced by inserting DNA encoding Fabs of the antibody into a vector for prokaryotic expression system, or for eukaryotic expression system, and introducing the vector into a procaryote or eucarycote (as appropriate) to express the Fabs.

Similarly, F(ab')2 fragments of the present invention can be obtained treating an antibody which specifically reacts with GAL1 with a protease, pepsin. Also, the F(ab')2 fragment can be produced by binding Fab' described below via a thioether bond or a disulfide bond.

Fab' fragments of the present invention can be obtained treating F(ab')2 which specifically reacts with hGAL1 with a reducing agent; dithiothreitol. Also, the Fab' fragments can be produced by inserting DNA encoding a Fab' fragment of the antibody into an expression vector for prokaryote, or an expression vector for eukaryote, and introducing the vector into a prokaryote or eukaryote (as appropriate) to perform its expression.

In addition, scFvs of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure. (see, e.g., WO98/45322; WO 87/02671: U.S. Pat. Nos. 5,859,205; 5,585,089; 4,816,567; EP0173494).

V. Modification of Antibodies, Immunoglobulins, and Polypeptides

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive, capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In one embodiment, amino acid changes may be achieved by changing cc dons in the DNA sequence to encode conservative substitutions based on conservation of the genetic code. Specifically, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code,

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in an organisms (although certain organisms may translate some sequences more efficiently than they do others). Moreover, occasionally, a methylated variant: of a purine or pyrimidine may be found in a given nucleotide sequence. Such methylations do not greet the coding relationship between the trinucleotide codon and the corresponding amino acid.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein; which in turn defines the interaction of the protein with other molecules, for example; enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8):

cysteine/cystine (+2.5); methionine (±1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups; (c) free sulfhydryl groups such as those of cysteine, (d) free hydroxyl groups such as those of serine, threonine, or hydroxyproline, (e) aromatic residues, such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine, or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Other modifications can involve the formation of immunoconjugates. For example, in one type of covalent notification, antibodies or proteins are covalently linked to one of a variety of non proteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimide (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), his-azido compounds (such as bis(p-azidobenzoyl)hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

VI. Uses and Methods of the Invention

The anti-Gal1 antibodies, immunoglobulins, polypeptides, and nucleic acids of the present invention described herein can be used in numerous predictive medicine assays (e.g., diagnostic assays, prognostic assays, and monitoring clinical trials) based on detection of Gal1 expression. The term "detection" as used herein includes qualitative and/or quantitative detection (measuring levels) with or without reference to a control. As described herein, a Gal1 polypeptide or fragment thereof of the present invention has one or more of the following activities: 1) binds to and/or modulates the activity of its natural binding partner(s), 2) modulates intra- or intercellular signaling, 3) modulates activation and/or proliferation of lymphocytes, 4) modulates the immune response of an organism, e.g., a mammalian organism, such as a mouse or human, and 5) modulates hypoxia associated angiogenesis. Sec, for example, Toscano et al. (2007) *Cyt Growth Fact Rev* 18:57-71; Camby et al. (2006) *Glycobiol* 16:137R-157R, each of which is incorporated herein, by reference, in its entirety.

Thus, one aspect of the present invention relates to diagnostic assays for determining Gal1 polypeptide expression in the context of a biological sample (e.g., blood, serum, cells, or tissue) to thereby determine the level of Gal1 polypeptide in the sample, to determine whether an individual is afflicted with a disorder and/or to determine the state of such a disorder, indicated by such Gal1 levels. For example, antibodies of the present invention are useful for staging cancer diseases associated with aberrant Gal1 expression.

The present invention also provides for prognostic (or predictive) assays for determining, whether an individual is at risk of developing such a disorder. Another aspect or the present invention pertains to monitoring the influence of agents (e.g., drugs, compounds) on the expression or activity of Gal1 in clinical trials.

In any method described herein, Gal1 expression can be detected either alone or in combination with the expression of other molecules. As described in the Examples, for instance, Gal1 is aberrantly co-expressed with other immunoinhibitory molecules, such as PD-L1. Combinatorial detection (e.g., sequentially or simultaneously) of several molecules can provide useful information regarding synergies of therapeutic intervention and/or personalized, higher-resolution diagnoses of disorder subtypes. In some embodiments, Gal1 is combinatorially detected with one more markers selected from the group consisting of PD-L1, PD-L2, PD-1, CTLA-4, B7-1, B7-2, CD28, ICOS, and ICOS-L.

1. Diagnostic Assays

The present invention provides, in part, methods, systems, and code for accurately classifying whether a biological sample expresses Gal1 and/or the levels of Gal1 are modulated Gal1 (e.g., upregulated or downregulated), thereby indicative of the state of a disorder of interest, such as cancer. In some embodiments, the present invention is useful for classifying a sample (e.g., From a subject) as associated with or at risk for cancer or a subtype thereof, mediated by Gal1 (known as a Gal1 sample) and using a statistical algorithm and/or empirical data (e.g., the presence, absence, or level of Gal1).

An exemplary method for detecting the level of expression or activity of Gal1 or fragments thereof, and thus useful for classifying whether a sample is associated with a disease or disorder mediated by Gal1 or a clinical subtype thereof involves obtaining a biological sample from a test subject and contacting the biological sample with an antibody or antigen-binding fragment thereof of the present invention capable of detecting Gal1 such that the level of expression or activity of Gal1 is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a Gal1 sample based upon a prediction or probability value and the presence or level of Gal1. The use of a single learning statistical classifier system typically classifies the sample as a Gal1 sample with a sensitivity specificity, positive predictive value, negative predictive value and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures; perceptions such as multi-layer perceptions, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g. Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the Gal1 sample classification results to a clinician, e.g., a histopathologist or an oncologist.

In another embodiment, the method of the present invention further provides a diagnosis in the form of a probability that the individual has a condition or disorder associated with aberrant expression or activity of Gal1. For example, the individual can have about a 0%, 5%, 10%, 15%, 20%, 25%, 30%, 35%, 40%, 45%, 50%, 55%, 60%, 65%, 70%, 7.5%, 80%, 85%, 90%, 95%, or greater probability of having the condition or disorder. In yet another embodiment, the method of the present invention further provides a prognosis of the condition or disorder in the individual. In some instances, the method of classifying a sample as a Gal1 sample is further based on the symptoms (e.g., c finical factors) of the individual from which the sample is obtained. The symptoms or group of symptoms can be, for example, lymphocyte count, white cell count, erythrocyte sedimentation rate, diarrhea, abdominal pain, cramping, fever, anemia, weight loss, anxiety, depression, and combinations thereof. In some embodiments, the diagnosis of an individual as having a condition or disorder associated with aberrant expression or activity of Gal1 is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by Gal1), a biological sample from the subject during remission or before developing a condition or disorder mediated by Gal1, or a biological sample from the subject during treatment for developing a condition or disorder mediated by Gal1.

An exemplary method for detecting the presence or absence of Gal1 polypeptide or fragments thereof is an antibody of the present invention, or fragment thereof, capable of binding to a Gal1 polypeptide, preferably an antibody with a detectable label. Antibodies can be polyclonal, or more preferably, monoclonal. Such agents can be labeled. The term "labeled", with regard to the antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells, and biological fluids isolated from a subject, such as serum, as well as tissues, cells, and fluids present within a subject. That is, the detection method of the present invention can be used to detect Gal1, or fragments thereof, in a biological sample in vitro as well as in vivo. In vitro techniques for detection of Gal1 polypeptide include enzyme linked immunosorbent assays (ELISAs), Western blots, immunoprecipitations, immunohistochemistry (IHC), intercellular flow cytometry and related techniques, and immunofluorescence; Furthermore, in vitro techniques for detection of a Gal1 polypeptide or a fragment thereof include introducing into a subject a labeled anti-Gal1 antibody. For example, the antibody can be labeled with a radioactive, luminescent, fluorescent, or other similar marker whose presence and location in a subject can be detected by standard imaging techniques.

In one embodiment, the biological sample contains polypeptide molecules from the test subject. A preferred biological sample is a serum, tumor microenvironment, perituoral or intratumoral, isolated by conventional means from a subject.

In another embodiment, the methods further involve obtaining a control biological sample from a control subject, contacting the control sample with a compound or agent capable of detecting Gal1 polypeptide, or fragments thereof such that the presence of Gal1 polypeptide or fragments thereof, is detected in the biological sample, and comparing the presence of Gal1 polypeptide, or fragments thereof, in the control sample with the presence of Gal1 polypeptide, or fragments thereof in the test sample.

In still other embodiments, the antibodies can be associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of Gal1 by use of an immunochromatographic or immunochemical assay such as in a "sandwich" or competitive assay. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" Gal1 polypeptides in a biological sample and the captured (or immobilized) Gal1 polypeptides may be bound to a labeled form of an anti-Gal1 antibody of the invention for detection. Other standard embodiments of immunoassays are well known the skilled artisan, including assays based on, for example, immunodiffusion, immunoelectrophoresis, immunohistopathology, immunohistochemistry, and histopathology.

2. Prognostic Assays

The diagnostic methods described herein can furthermore be utilized to identify subjects having or at risk of developing a disorder associated with aberrant or undesired Gal1 expression levels. As used herein, the term "aberrant" includes a Gal1 expression or activity which deviates from the wild type or normal Gal1 expression or activity. Aberrant expression or activity includes increased or decreased expression or activity, as well as expression or activity which does not follow the wild type developmental pattern of expression or the subcellular pattern of expression. For example, aberrant Gal1 expression or activity is intended to include the cases in which a mutation in the Gal1 gene or regulatory sequence thereof causes the Gal1 gene to be underexpressed or over-expressed and situations in which such mutations result in a non-functional Gal1 polypeptide or a polypeptide which does not function in a wild-type fashion, e.g., a polypeptide which does not interact with a Gal1 binding partner(s) or one which interacts with a non-Gal1 binding partner(s). As used herein, the term "unwanted" includes an unwanted phenomenon involved in a biological response such as immune cell activation. For example, the term unwanted includes a Gal1 expression or activity which is undesirable in a subject.

Many disorders associated with aberrant Gal1 expression are known to the skilled artisan, as explained further in the Examples. Gal1 is expressed by multiple tumor types, including select lymphoid malignancies, virally-induced cancers, and many solid tumors. In some embodiments, the disorder is a lymphoid malignancy subtype, such as one or more of AP-1-dependent lymphoid malignancies (e.g., classical Hodgkin lymphoma (cHL) and anaplastic large cell lymphoma (ALCL)) and MLL-rearranged ALL. In one study, all primary MLL-rearranged ALLs were Gal1 positive regardless of translocation partner, whereas only 2 of 81 germline MLL-rearranged ALLs expressed Gal1 (Juszczynski et al. (2010) Clin. Cancer. Res. 16:2122-2130). In other embodiments, the disorder is a virally-induced malignancy, such as one or more of EBV-positive post transplant lymphproliferative disorder (PTLD), nasopharyngeal carcinoma, and Kaposi's sarcoma. In still other embodiments, the disorder is a solid tumor, such as one or more of breast cancer, prostate cancer, lung cancer, pancreatic cancer, squamous cell carcinoma of the head and neck, hepatocellular carcinoma, and melanoma. Generally, Gal1 expression is an adverse prognostic marker in all of these solid tumors. For example, silencing of Gal1 is associated with anti-tumor effects in breast cancer, prostate cancer, lung cancer, and melanoma.

The assays described herein, such as the preceding diagnostic assays or the following assays, can be utilized to identify a subject having or at risk of developing a disorder associated with a misregulation of Gal1 polypeptide expression. Thus, the present invention provides a method for identifying a disorder associated with aberrant or unwanted Gal1 expression in Which a test sample is obtained from a subject and Gal1 polypeptide is detected, wherein the presence of Gal1 polypeptide is diagnostic for a subject having or at risk of developing the disorder associated with aberrant or unwanted Gal1 expression or activity. As used herein, a "test sample" refers to a biological sample obtained from a subject of interest. For example, a test sample can be a biological fluid (e.g., cerebrospinal fluid or serum), cell sample, or tissue, such as a histopathological slide of the tumor microenvironment, perimtural area, and/or intratumoral area.

Furthermore, the prognostic assays described herein can be used to determine whether a subject can be administered an agent(e.g., an agonist, antagonist, peptidomimetic, polypeptide, peptide, nucleic acid, small molecule, or other drug candidate) to treat such a disorder associated with aberrant or unwanted Gal1 expression or activity. For example, such methods can be used to determine whether a subject can be effectively treated with one or a combination of agents. Thus, the present invention provides methods for determining whether a subject can be effectively treated with one or more agents for treating a disorder associated with aberrant or unwanted Gal1 expression in which a test sample is obtained and Gal1 polypeptide is detected (e.g., wherein the abundance of Gal1 polypeptide expression is diagnostic for a subject that can be administered the agent to treat the disorder associated with aberrant or unwanted Gal1 expression).

The methods described herein may be performed, for example, by utilizing, pre-packaged diagnostic kits comprising at least one antibody reagent described herein, which may be conveniently used, e.g., in clinical settings to diagnose patient exhibiting symptoms or family history of a disease or illness involving Gal1.

Furthermore, any cell type or tissue in which Gal1 is expressed may be utilized in the prognostic assays described herein.

Another aspect of the present invention includes uses of the compositions, and methods described herein for association and/or stratification analyses in which the expression of Gal1 in biological samples from individuals with a disorder associated with aberrant Gal1 expression, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is ease-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-contort studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and Clinical data of the samples can be summarized by descriptive statistics with tables and graphs well known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.2 (a significance level on the lenient side), for example, may be used for generating hypotheses for significant association of a Gal1 expression level with certain phenotypic characteristics of a disease. It is preferred that a p-value <0.05 (a significance level traditionally used in the art) is achieved in order for the level to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme can be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

3. Monitoring of Effects, During Clinical Trials

Monitoring the influence of agents (e.g., compounds, drugs or small molecules) on the expression or activity of a Gal1 polypeptide or a fragment thereof (e.g., the modulation of cell proliferation and/or migration) can be applied not only in basic drug screening, but also in clinical trials. For example, the effectiveness of au agent determined by a screening assay as described herein to decrease Gal1 gene expression, polypeptide levels, or downregulate Gal1 activity, can be monitored in clinical trials of subjects exhibiting decreased Gal1 gene expression, polypeptide levels, or downregulated Gal1 activity. In such clinical trials, the expression or activity of a Gal1 gene and/or symptoms or markers of the disorder of interest, can be used as a "read out" or marker of the phenotype of a particular cell, tissue, or system.

For example, and not by way of limitation, genes, including Gal1 that are modulated in cells by treatment with an agent compound, drug or small molecule) which modulates Gal1 activity (e.g. identified in a screening assay as described herein) can be identified. Thus, to study the effect of agents on a disorder associated with aberrant Gal1 expression, for example, in a clinical trial, cells can be isolated and nucleic acids and/or protein prepared and analyzed for the levels of expression of Gal1 and/or other genes implicated in the disorder associated with aberrant Gal1 expression. The levels of gene expression (e.g., a gene expression pattern) analyzed by measuring the amount of polypeptide produced, by one of the methods as described herein, or by measuring the levels of activity of Gal1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) Obtaining a pre-administration sample from a subject prior to administration of the agent; (ii) detecting the level of expression of a Gal1 polypeptide, or fragments thereof, in the pre administration sample; (iii) obtaining one or mom post-administration samples from the subject; (iv) detecting the level of expression of the Gal1 polypeptide, or fragments thereof, in the post-administration samples; (v) comparing the level of expression or activity of the Gal1 polypeptide, or fragments thereof, in the pre-administration sample with the Gal1 polypeptide, mRNA, or genomic DNA in the post administration sample or samples; and (vi) altering the administration of the agent to the subject accordingly. For example, increased administration of the agent may be desirable to decrease the expression or activity of Gal1 to lower levels than detected, i.e., to increase the effectiveness of the agent. According to such an embodiment, Gal1 expression or activity may be used as an indicator of the effectiveness of an agent, even in the absence of an observable phenotypic response.

VII. Kits

In addition, the present invention also encompasses kits for detecting the presence of a Gal1 polypeptide, or fragments thereof, in a biological sample. For example, the kit can comprise a labeled compound or agent capable of detecting a Gal1 polypeptide, or fragments thereof, in a biological sample; means for determining the amount of the Gal1 polypeptide, or fragments thereof, in the sample; and means for comparing the amount of the Gal1 polypeptide, or fragments thereof, in the sample with a standard. The compound or agent can be packaged in a suitable container. For example, the present invention provides kits comprising at least one antibody described, herein. Kits containing antibodies of the invention find use in detecting Gal1 expression or diagnostic assays. Kits of the invention can contain an antibody coupled to a solid support, e.g., a tissue culture plate or beads (e.g., sepharose beads).

A kit can include additional components to facilitate the particular application for which the kit is designed. For example, kits can be provided which contain antibodies for detection and quantification of Gal1 in vitro, e.g. In an ELISA or a Western blot. Additional, exemplary agents that kits can contain include means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or Gal1 protein standards). A kit may additionally include buffers and other reagents recognized for use in a method of the disclosed invention. Non-limiting examples include agents to reduce non-specific binding such as a carrier protein or a detergent. A kit of the present invention can also include instructional materials disclosing or describing the use of the kit or an antibody of the disclosed invention in a method of the disclosed invention as provided herein.

This invention is further illustrated by the following examples which should not be construed as limiting. The contents of all references, patents and published patent applications cited throughout this application, as well as the Figures, are incorporated herein by reference.

EXAMPLES

Example 1: Anti-Gal1 Monoclonal Antibodies Useful for Diagnostic Applications

Figure 2:
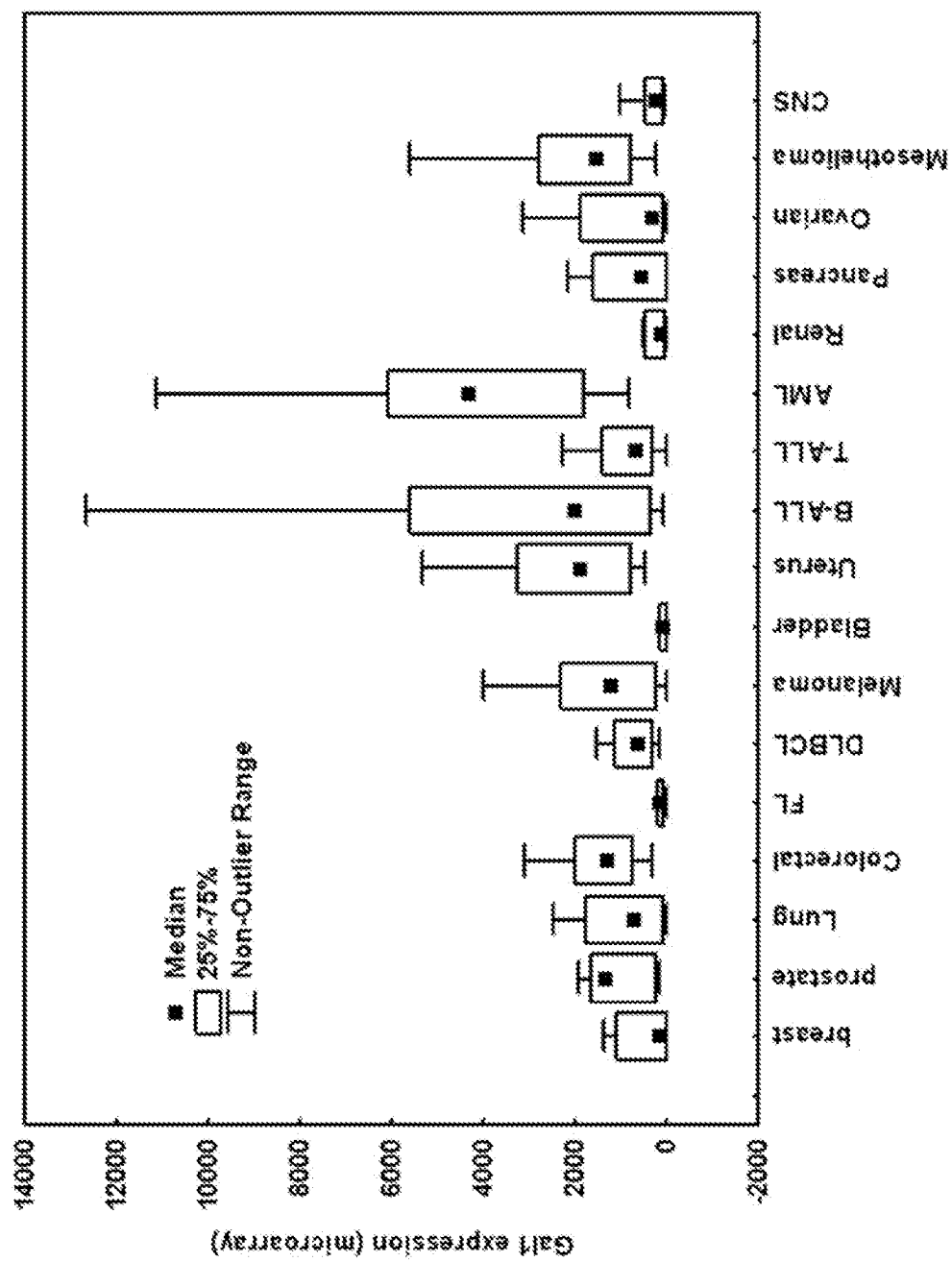
FIG. 2 shows Gal1 expression (transcript abundance) in multiple solid and hematologic malignancies, Gal1 transcript abundance is highly increased in multiple tumor types, including select lymphoid malignancies, virally-induced cancers, and many solid rumors.

Anti-Gal1 monoclonal antibodies were generated and were determined to cross-react well with both human Gal1 and mouse Gal1 (FIG. 1). Epitope mapping indicated that the 8A12.H9.H10 (i.e., the 8A12) anti-Gal1 monoclonal antibody recognized a domain distal to the previously described carbohydrate-binding domain (CBD) of Gal1 and encompasses a kappa light chain. Six recombinant human Gal1 fragments (covering the N-terminal, CBD, post-CBD sequences) named F1, F2, F3, F4, F5, F6 and the full length protein F7 in fusion with GST-tag were produced in E. coli (FIG. 2). The 8A12 monoclonal antibody was determined to recognize recombinant GST-F5, GST-F6 and GST-F7 by Western blot analysis, but none of GST-F1, GST-F2, GST-F3 and GST-F4, indicating that the antibody binds to the post-CBD domain.

The 8A12 antibody was sequenced, which are presented in Table 1 below, and analysis of the sequences obtained from the hybridomas is summarized in Table 1 below. In addition, hybridoma cell line 8A12 was deposited with the American Type Culture Collection (ATCC) and was received on Jul. 2, 2013 in accordance with the provisions of the Budapest Treaty on the International Recognition of the Deposit of Microorganisms for the Purposes of Patent Procedure under deposit number PTA-120449.

TABLE 1

Identification and sequencing of the leader and viariable regions of anti-human Gal1 monoclonal antibodies, 8A12

8A12 Light Chain Variable (vK) DNA and Amino Acid Sequences*
LOCUS 8A12H9H10_VK 396 bp DNA linear

| FEATURES | Location/Qualifiers |
|---|---|
| J_segment | 367 . . . 396 |
|  | /label = JK |
| V_segment | 340 . . . 366 |
|  | /label = CDR-L3 |
| V_region | 244 . . . 339 |
|  | /label = FWR3 |
| V_segment | 223 . . . 243 |
|  | /label = CDR-L2 |
| V_region | 178 . . . 222 |
|  | /label = FWR2 |

TABLE 1-continued

Identification and sequencing of the leader and viariable regions of anti-human Gal1 monoclonal antibodies, 8A12

|   |   |
|---|---|
| V_segment | 130 ... 177 /label = CDR-L1 |
| V_region | 61 ... 129 /label = FWR1 |
| sig_peptide | 1 ... 60 /label = LS |
| CDS | 1 ... 396 /label = 9H10\VK |

/translation="MMSPAQFLFLLVLWIQKTNGDVVMTQTPLTLSVTIGQPAS

ISC<u>KSSQSLLDSDGKTYLN</u>WLLQRPGQSPKRLIY<u>LLSKLDS</u>GVPDRFTGSGSGT

DFTLQISRVEAEDLGFYYC<u>WQGTHFPYT</u>FGGGTKLEIK" (SEQ ID NO: 5)

BASE COUNT    102 a    88 c    99 g    107 t
ORIGIN
(SEQ ID NO: 6)
```
  1 atgatgagtc ctgcccagtt cctgtttctg ttagtgctct ggattcagaa aaccaacggt
 61 gatgttgtga tgactcagac cccactcact ttgtcggtta ccattggaca accagcctcc
121 atctcttgca agtcaagtca gagcctctta gatagtgatg gaaagacata tttgaattgg
181 ttgttacaga ggccaggcca gtctccaaag cgcctaatct atctgctgtc taaactggac
241 tctggagtcc ctgacaggtt cactggcagt ggatcaggga cagatttcac actgcaaatc
301 tacacgttcg gagggggac caagctggaa ataaaa
```

SEQ ID NO: 9 Signal Peptide (base pairs 1-60):

1 ATGATGAGTCCTGCCCAGTTCCTGTTTCTGTTAGTGCTCTGGATTCAGAAAACCAACGGT 60

SEQ ID NO: 10 Framework 1 (base pairs 61-129):

61GATGTTGTGATGACTCAGACCCCACTCACTTTGTCGGTTACCATTGGACAACCAGCCTCCATCTCTTG
C 129

SEQ ID NOs: 11-12, respectively CDR-L1 (base pairs 130-177):

130 AAGTCAAGTCAGAGCCTCTTAGATAGTGATGGAAAGACATATTTGAAT 177
    K   S   S   Q   S   L   L   D   S   D   G   K   T   Y   L   N

SEQ ID NO: 13 Framework 2 (base pairs 178-222):

178 TGGTTGTTACAGAGGCCAGGCCAGTCTCCAAAGCGCCTAATCTAT 222

SEQ ID NO: 14-15, respectively CDR-L2 (base pairs 223-243):

223 CTGCTGTCTAAACTGGACTCT 243
    L   L   S   K   L   D   S

SEQ ID NO: 16 Framework 3 (base pairs 244-339):

244GGAGTCCCTGACAGGTTCACTGGCAGTGGATCAGGGACAGATTTCACACTGCAAATCAGCAGAGTGG
AGGCTGAGGATTTGGGATTTTATTATTGC 339

SEQ ID NO: 17-18, respectively CDR-L3 (base pairs 340-366);

340 TGGCAAGGTACACATTTTCCTTACACG 366
    W   Q   G   T   H   F   P   Y   T

SEQ ID NO: 19 J Segment (base pairs 367-396):

367 TTCGGAGGGGGGACCAAGCTGGAAATAAAA 396

8A12 Heavy Chain Variable (vH) DNA and Amino Acid Sequences*
LOCUS 8A12H9H10_VH 393 bp DNA linear

| FEATURES | Location/Qualifiers |
|---|---|
| J_segment | 361 ... 393 /label = JH |
| V_segment | 352 ... 360 /label = CDR-H3 |
| V_region | 256 ... 351 /label = FWR3 |
| V_segment | 205 ... 255 /label = CDR-H2 |
| V_region | 163 ... 204 /label = FWR2 |

TABLE 1-continued

Identification and sequencing of the leader and viariable regions of anti-human Gal1 monoclonal antibodies, 8A12

| | | |
|---|---|---|
| V_segment | 148 . . . 162 | |
| | /label = CDR-H1 | |
| V_region | 58 . . . 147 | |
| | /label = FWR1 | |
| sig_peptide | 1 . . . 57 | |
| | /label = LS | |
| CDS | 1 . . . 393 | |
| | /label = 8A12H9H10\VH | |

/translation="MGWSGIFLFLLSVTTGVHSQAYLQQSGAELVRPGASVRMS

CKASGYTFT<u>RYNMH</u>WVKQTPRQGLEWIG<u>RIYPGNGDTSYNQKFKG</u>KATLTVDKS

SSTAYMQLSSLTSEDSAVYFCTV<u>WDY</u>GQGTTLTVSS" (SEQ ID NO: 7)

BASE COUNT     95 a     105 c     101 g     92 t
ORIGIN
                                                          (SEQ ID NO: 8)
  1 atgggatgga gcgggatctt tctcttcctc ctgtcagtaa ctacaggtgt ccactcccag
 61 gcttatctac agcagtctgg ggctgagctg gtgaggcctg gggcctcagt gaggatgtcc
121 tgcaaggctt ctggctacac tttcaccagg tacaatatgc actgggtaaa gcagacacct
181 agacagggcc tggaatggat tggacgtatt tatccaggaa atggtgatac ttcctacaat
241 cagaagttca agggcaaggc cacactgact gtagacaaat cctccagcac agcctacatg
301 cagctcagca gcctgacatc tgaagactct gcggtctatt tctgtacagt ctgggactac
361 tggggccaag gcaccactct cacagtctcc tca SEQ ID NO: 20 Signal Peptide (base pairs 1-57):

1 ATGGGATGGAGCGGGATCTTTCTCTTCCTCCTGTCAGTAACTACAGGTGTCCACTCC 57

SEQ ID NO: 21 Framework 1 (base pairs 58-147):

58CAGGCTTATCTACAGCAGTCTGGGGCTGAGCTGGTGAGGCCTGGGGCCTCAGTGAGGATGTCCTGCAA
GGCTTCTGGCTACACTTTCACC 147

SEQ ID NOs: 22-23, respectively CDR-H1 (base pairs 148-162);

148 AGGTACAATATGCAC 162
    R  Y  N  M  H

SEQ ID NO: 24 Framework 2 (base pairs 163-204):

163 TGGGTAAAGCAGACACCTAGACAGGGCCTGGAATGGATTGGA 204

SEQ ID NOs: 25-26, respectively CDR-H2 (base pairs 205-255);

205 CGTATTTATCCAGGAAATGGTGATACTTCCTACAATCAGAAGTTCAAGGGC 255
    R  I  Y  P  G  N  G  D  T  S  Y  N  Q  K  F  K  G

SEQ ID NO: 27 Framework 3 (base pairs 256-351):

256AAGGCCACACTGACTGTAGACAAATCCTCCAGCACAGCCTACATGCAGCTCAGCAGCCTGACATCTG
AAGACTCTGCGGTCTATTTCTGTACAGTC 351

CDR-H3 (base pairs 352-360):

352 TGGGACTAC 360 (cDNA: nucleotides 352-360 of SEQ ID NO: 8)
    W  D  Y    (polypeptide: amino acid residues 118-120 of SEQ ID NO: 7)

SEQ ID NO: 28 J Segment (base pairs 361-393):

361 TGGGGCCAAGGCACCACTCTCACAGTCTCCTCA 393

*CDR definitions and protein sequence numbering according to Kabat. CDR amino acid sequences are underlined in order of CDR1, CDR2, and CDR3, respectively.

Example 2: Gal1 Serum Levels in Classical Hodgkin Lymphoma (cHL)

A. Patients and Samples

For the retrospective study, frozen serum samples and clinical data from 293 newly diagnosed, previously untreated cHL patients were used from patients who were enrolled on Institutional Review Board-approved risk-adapted German Hodgkin Study Group (GHSG) multicenter clinical trials: a) HD13 (ISRCTN63474366) for early-stage disease (clinical stage [CS] IA-IIB with no risk factors, 80 patients) (Diehl et. al. (2003) *Hematol. Am. Soc. Hematol. Educ. Program Rev.* 2003:225-247; Sieniawski et al. (2007) *J. Clin. Oncol.* 25:2000-2005); b) HD14 (IS-RCTN04761296) for early-stage disease with risk factors (CS I-IIA with large mediastinal mass, extranodal disease, elevated erythrocyte sedimentation rate (ESR) or ≥3 nodal areas and CS IIB with elevated ESR or ≥3 nodal areas, 89 patients) (Diehl et al. (2003) *Hematol. Am. Soc. Hematol. Educ. Program Rev.* 2003:225-247; von Tresckow et al.

(2012) *J. Clin. Oncol.* 30:907-913): and c) HD18 (NCT00515554) for bulky localized or advanced-stage disease (CS IIB with bulky mediastinal involvement and/or extranodal involvement and CS III or IV, 124 patient) (Diehl et al. (2003) *Hematol. Am. Soc. Hemotol. Educ. Program Rev.* 2003:225-747; see the study, HD18 for advanced stages in Hodgkin lymphoma, available on the World Wide Web at clinicaltrials.gov/ct2/show/NCT00515554). In addition, serum samples from 15 healthy normal donors were prepared by centrifuging clotted peripheral blood at 2,500 rpm for 20 min.

B. Gal1 Sandwich ELISA

An anti-Gal1 rabbit polyclonal antibody (capture antibody) and a biotin-coupled murine monoclonal antibody, 8A12 (detection antibody), were generated (Rodig et al. (2008) *Clin. Cancer. Res.* 14:3338-3344: Ouyang et al. (2011) *Blood* 117:4315-4322) and determined to have optimal sensitivity and signal-to-noise ratio. Serum Gal1 levels were assessed according to a standard sandwich ELISA protocol. In brief, 96-well EIA/RIA microplates (Fisher Scientific, Pittsburgh. Pa.) were pre-coated with capture antibody at 4 µg/mL (100 µL/well, diluted in 0.05 mol/L carbonate-bicarbonate buffer) at 4° C. overnight. After 3 washes with PBS/0.05% Tween-20 (Sigma-Aldrich, St. Louis, Mo.), the plate was treated with blocking buffer (1% BSA in PBS/0.05% Tween-20) at room temperature (RT) for 1 h. Scrum-free conditioned media (SFCM) from a Gal1$^+$ HL line, L428, and a serum sample from a healthy normal donor (ND#1) were used as controls in each ELISA plate. All samples were diluted (serum samples, 1:16; L428 SFCM, 1:32) and added in duplicates and incubated at RT for 2 h. After the incubation with detection antibody, biotinylated 8A12 (1:1000), at RT for 2 h, 100 µl of strepavidin-horseradish peroxidase (1:15,000, Thermo Scientific, Rockford, Ill.) was added for incubation RT for 20 min. After 5 washes, the reaction was developed by 100 µl of 1-step turbo TMB (Thermo Scientific) and stopped by 1 mol/L $H_2SO_4$. Absorbance at 450 and 570 nm were determined in SpectraMax M3 Absorbance Microplate Reader (Molecular Device Inc. Sunnyvale, Calif.). A standard curve of recombinant His-tagged Gal1 (rGal1) at concentrations of 80 to 0.312 ng/ml with 1:2 serial dilutions (9 points total) was generated and fitted using a four-parameter nonlinear regression curve for each ELISA. Sample concentrations were calculated by regression analysis using the standard curve.

C. Statistical Analysis

Data analysis was carried out using SAS version 9.2. A receiver-operating characteristic (ROC) curve was plotted to determine the cut-off values for normal versus elevated serum Gal1. Because of skewed distributions, non-parametric analyses of serum Gal1 values were performed using Wilcoxon two-sample test or Kruskal-Wallis test for group comparisons. Univariate analyses included Ann Arbor stage (I-IV), number of involved nodal sites (≥3), presence of B symptoms, extranodal disease and elevated ESR, all of which are well-established parameters of HL tumor burden. Serum Gal1 levels were also analyzed with respect to male sex, age of 45 years or older, state IV disease, low serum albumin, leukocytosis and lymphocytopenia, because of the prognostic relevance of these factors in the International Prognostic Score (IPS) (Hasenclever and Diehl (1998) *N. Engl. J. Med.* 339:1506-1514; Moccia et al. (2012) *J. Clin. Oncol.* 30:3383-3388) for advanced-stage HL. Nominal p-values are presented.

D. Results

Figure 3:
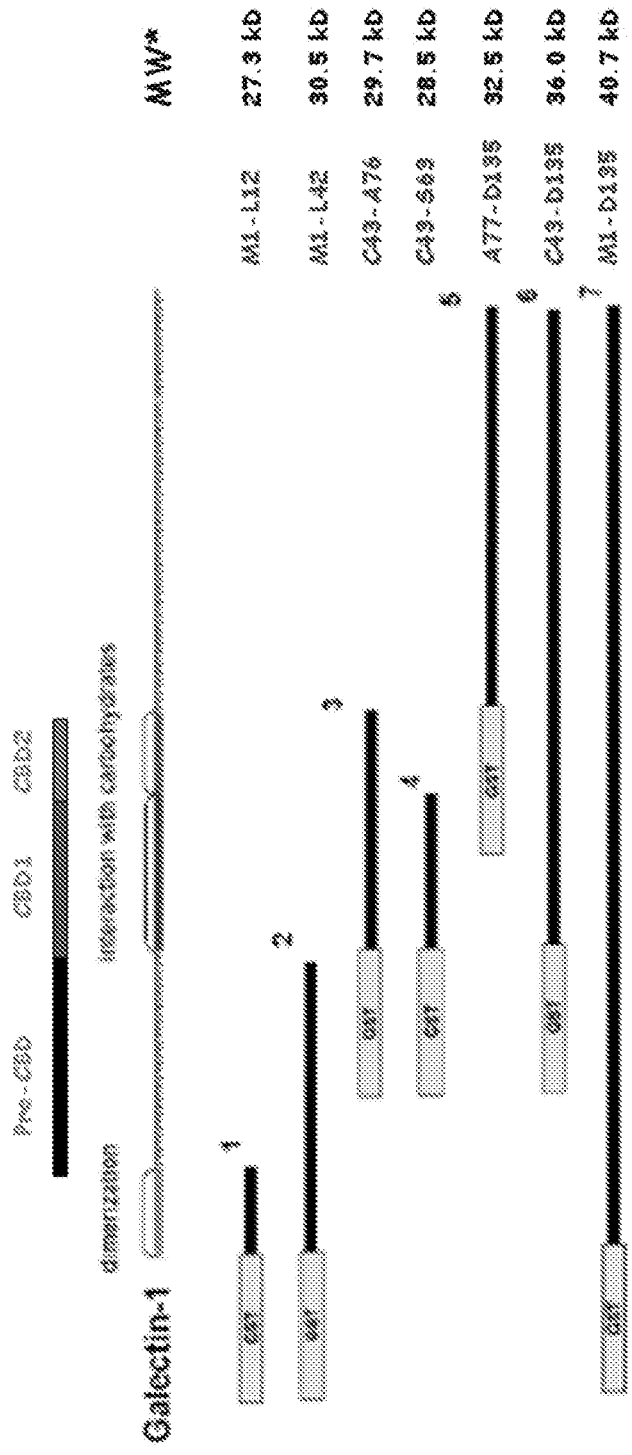
FIG. 3 shows a schematic of recombinant GST-tagged human Gal1 and fragments is shown.
Figure 4:
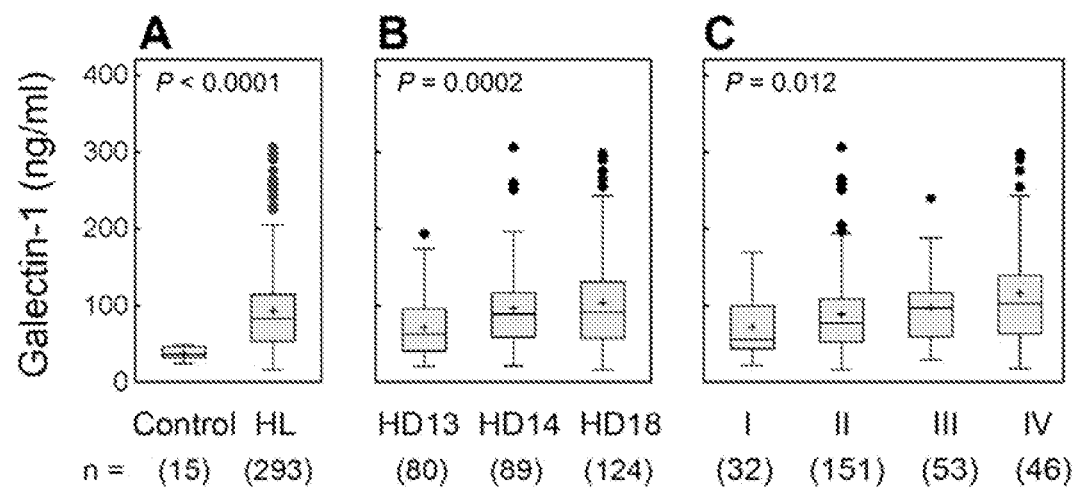
FIGS. 4A-4C show that serum levels of Gal1 are significantly higher in cHL samples relative to normal controls and are associated with clinical parameters of tumor burden in cHL patients. Gal1 serum levels were assessed with a sandwich ELISA.

Gal1 protein expression and transcript abundance are highly correlated and Gal1 is expressed by multiple tumor types, including select lymphoid malignancies, virally-induced cancers, and many solid tumors (FIG. 3). Thus, there is a need for reagents that can detect Gal1 polypeptides and fragments thereof, particularly those reagents that perform well established diagnostic assays, such as immunohistochemistry (IHC) and ELISA assays. Thus, a sandwich ELISA with purified rGal1 was established and newly developed Gal1 antibodies used therein (see Example 1) were applied to determine the levels of serum Gal1 in 15 healthy normal donors and 293 newly diagnosed, previously untreated cHL patients from the GHSG. The data demonstrate that serum levels of Gal1 are significantly higher in cHL samples relative to normal controls and are associated with clinical parameters of tumor burden in cHL patients. Specifically, serum Gal1 levels were significantly elevated in cHL patients in comparison to normal controls ($p<0.0001$) (FIG. 4A). By plotting a ROC curve, it was determined that a cut-off value of 49.9 ng/ml distinguished Gal1 serum levels of cHL patients from those of normal donors with 100% specificity and 76.5% specificity. Patients enrolled on the HD13 trial (for early-stage low-risk disease), had significantly lower Gal1 levels than patients on HD14 (for early stage disease with additional risk factors) or HD18 (for bulky localized or advanced-stage disease) (HD13 vs. HD14 vs, HD18, p=0.0002) (FIG. 4B and Table 2).

TABLE 2

GHSG trials, cHL patient characteristics and association with serum Gal1 levels

A. GHSG trials

| Trial | Risk group | Patients | (%) | Gal1 (ng/ml)* | P Value |
|---|---|---|---|---|---|
| HD13 | Favorable | 80 | (27.3) | 71.6 ± 39.7 | |
| HD14 | Intermediate | 89 | (30.4) | 97.4 ± 54.3 | 0.0002 |
| HD18 | Unfavorable | 124 | (42.3) | 103.7 ± 63.4 | |
| Total | | 293 | (100) | 93.0 ± 56.5 | |

B. Patient characteristics and association with serum Gal1 levels

| Variable | Patients | (%) | Gal1 (ng/ml)* | P Value |
|---|---|---|---|---|
| All patients | 293 | (100) | 93.0 ± 56.5 | |
| Age | | | | n.s. |
| ≥45 yr | 65 | (22.2) | 62.8 ± 43.0 | |
| <45 yr | 228 | (77.8) | 90.4 ± 55.9 | |
| Gender | | | | n.s. |
| Male | 156 | (53.2) | 92.8 ± 57.1 | |
| Female | 137 | (46.8) | 89.6 ± 53.6 | |
| Histologic type | | | | n.s. |
| Nodular sclerosis | 151 | (51.5) | 95.9 ± 55.9 | |
| Mixed cellularity | 64 | (21.8) | 96.2 ± 60.9 | |
| Lymphocyte-rich | 12 | (4.1) | 79.1 ± 43.3 | |
| Unclassified | 66 | (22.5) | 76.7 ± 43.8 | |
| Ann Arbor stage | | | | 0.012 |
| I | 32 | (10.9) | 72.7 ± 42.0 | |
| II | 151 | (51.5) | 88.9 ± 53.7 | |
| III | 53 | (18.1) | 96.5 ± 45.8 | |
| IV | 46 | (15.7) | 116.4 ± 76.5 | |
| Unknown# | 11 | (3.8) | | |
| B symptoms | | | | 0.047 |
| Absence | 168 | (57.3) | 85.3 ± 47.1 | |
| Presence | 114 | (38.9) | 104.1 ± 67.1 | |
| Unknown# | 11 | (3.8) | | |
| International prognostic score (IPS) | | | | 0.019 |
| 0 or 1 | 134 | (45.7) | 82.4 ± 44.0 | |
| 2-7 | 128 | (43.7) | 103.7 ± 66.0 | |
| Unknown# | 31 | (10.6) | | |

TABLE 2-continued

GHSG trials, cHL patient characteristics
and association with serum Gal1 levels

| Individual IPS risk factors | | | | |
|---|---|---|---|---|
| Extranodal involvement (stage IV) | | | | 0.011 |
| Absence | 249 | (85.0) | 89.2 ± 54.3 | |
| Presence | 35 | (11.9) | 116.3 ± 67.2 | |
| Unknown# | 9 | (3.1) | | |
| Lymphocyte count, <600/mm³ or <8% of toal white-cell count | | | | 0.036 |
| Absence | 269 | (91.8) | 91.2 ± 56.2 | |
| Presence | 13 | (4.4) | 124.9 ± 62.9 | |
| Unknown# | 11 | (3.8) | | |
| Additional prognostic factors | | | | |
| Number of involved lymph node sites ≥3 | | | | <0.0001 |
| Absence | 120 | (41.0) | 78.6 ± 49.0 | |
| Presence | 165 | (56.3) | 102.7 ± 59.6 | |
| Unknown# | 8 | (2.7) | | |
| Elevated erythrocyte sedimentation rate (ESR) | | | | 0.007 |
| Absence | 148 | (50.5) | 82.1 ± 45.3 | |
| Presence | 134 | (45.7) | 104.1 ± 65.6 | |
| Unknown# | 11 | (3.8) | | |

(A) Gal1 serum levels from cHL patients enrolled on the GHSG risk-adapted clinical trials, HD13, HD14 and HD18;
(B) Patient characteristics and association with Gal1 serum levels. Nominal p-values are presented;
*Mean ± SD;
Patients with unknown values were excluded from the indicated univariate analyses.

Next, the association of Gal1 serum levels with Ann Arbor stage and B symptoms, two major determinants for assigning HL patients to risk-adapted therapy (Lister et al. (1989) *J. Clin. Oncol.* 7:1630-1636), was determined. Gal1 levels increased with Ann Arbor stage (I vs. II vs. III vs. IV, p=0.012, FIG. 4C and Table 2: I-II vs, III-IV, p=0.006) and with B symptoms (p=0.047, Table 2).

The association of Gal1 levels with the HL IPS using the accepted groupings of IPS 0/1 vs. 2-7 was also determined (Hasenclever and Diehl (1998) *N. Engl. J. Med.* 339:1506-1514; Moccia et al. (2012) *J. Clin. Oncol.* 30:3383-3388). Patients with an IPS of 2-7 had significantly higher Gal1 levels than patients with an IPS of 0 or 1 (p=0.019) (Table 2). Increased Gal1 levels were also associated with 2 of 7 individual IPS risk factors (Hasenclever and Diehl (1998) *N. Engl. J. Med.* 339:1506-1514; Moccia et al. (2012) *J. Clin. Oncol.* 30:3383-3388): extranodal involvement (stage IV disease, p=0.011); and lymphocyte count <600 per mm³ or <8% of white cell count (p=0.036). Gal1 levels were also significantly elevated in cHL patients with 2 additional adverse prognostic factors (Hsi (2008) *Leuk. lymphoma* 49:1668-1680): ≥3 involved nodal sites (p<0.0001) and elevated ESR (p=0.007) (Table 2). Direct analyses of the association between Gal1 serum levels and outcome await completion of the ongoing HD18 clinical trial (see the study, HD18 for advanced stages in Hodgkin lymphoma, available on the World Wide Web at clinicaltrials.gov/ct2/show/NCT00515554).

Thus, Gal1 serum levels are elevated and associated with clinical features reflective of increased tumor burden in newly diagnosed cHL patients. Given the demonstrated role of Gal1 in tumor-immune escape, angiogenesis and metastasis, analyses of circulating Gal1 levels is expected to inform risk-adapted and targeted treatment strategies for cHL patients.

Example 3: Gal1 and PD-L1 are Co-Expressed by EBV- and HHV8-Associated Malignancies A. Case Selection Cases were retrieved from the surgical pathology files of Brigham and Women's Hospital, Boston, Mass.; Yale School of Medicine; New Haven Conn.; UMass Memorial Hospital, Worcester, Mass.; and from the consult files of a practitioner with institutional review board approval. Representative hematoxylin and eosin stained slides were reviewed. Whole tissue sections from EBV-positive of the elderly, EBV-positive immunodeficiency-related DLBCL, BL, ENKTCL, PBL, NPC, PEL, KS, and EBV-negative PTLD were evaluated. Seventy-seven total cases were evaluated for Gal1 expression by immunohistochemistry. Due to limited availability of tissue, a subset of these cases were evaluated for PD-L1 (59 cases), JunB (66 cases), and phosphorylated c-Jun (p-cJun; 63 cases) expression by immunohistochemistry. All cases of DLBCL, NPC, and BL were shown previously to be positive for EBV-encoded RNA (EBER) by in situ hybridization study. Nine of 11 PBL cases and 9/10 ENKTCL cases were positive for EBER. All EBV-negative PTLD cases were negative for EBER. All PEL cases and KS cases were shown previously to be positive for HHV8 by immunohistochemistry. Cases of DLBCL, NOS were evaluated as part of a tissue microarray, with each case arrayed in triplicate, as previously described in Kononen et al. (1998) *Nat. Med.* 4:844-847. Cases were confirmed to be EBV negative by an EBER situ hybridization assay.

B. Immunohistochemistry

Staining for Gal1, p-Jun, and JunB was performed using 4-µm-thick, formalin-fixed, paraffin-embedded tissue sections. Slides were baked, deparaffinized in xylene, passed through graded alcohols, and then antigen retrieved with either 10 mM citrate buffer, pH6.0 (Invitrogen, Carlsbad, Calif.), for Gal1 and JunB or 1 mM EDTA, pH 8.0 (Invitrogen), for p-cJun in a steam pressure cooker (Decloaking Chamber; BioCare Medical, Concord, Calif.) according to the manufacturer's instructions. All further steps were carried out at room temperature in a hydrated chamber. Slides were pretreated with Peroxidase Block (Dako North America, Carpinteria, Calif.) for 5 minutes to quench endogenous peroxidase activity, and then washed in 50 mM Tris-Cl, pH7.4. Slides were blocked using Protein Block (Dako) according to the manufacturer's instructions, and subsequently incubated with mouse anti-Gal1 (clone 8F4F8G7, 1:40000 dilution, final concentration 100 ng/mL) (Ouyana et al. (2011) *Blood* 117:4315-4322), rabbit anti-JunB (clone C37F9, 1:1000 dilution: Cell Signaling Technology, Beverly, Mass.), or rabbit anti-p-cJun (specific for phosphorylated serine at amino acid 63, clone 54B3, 1:50 dilution; Cell Signaling Technology) monoclonal antibodies in diluent (Dako) for 1 hour. Slides were then washed in Tris buffer and treated with anti-mouse or anti-rabbit horseradish peroxidase-conjugated antibody (Envision Plus; Dako) for 30 minutes. After further washing, immunoperoxidase staining was developed using a 3,3'diaminobenzidine (DAB) chromogen (Dako) for 5 minutes. Slides were counterstained with hematoxylin; dehydrated in graded alcohol and xylene, mounted and coverslipped.

Immunohistochemistry using a rabbit anti-PD-L1 monoclonal antibody (clone 15, final concentration of 6.2 µg/ml; Sino Biological, Beijing; China) was preformed using 4-µm-thick, formalin-fixed, paraffin-embedded tissue sections on a Benchmark X T autostainer (Ventana Medical Systems, Tuscon, Ariz.). UltraView Universal DAB Detection kit (Ventana) was used according to the manufacturer's instructions. IHC using the mouse anti-PD-L1 monoclonal antibody (IgG1, generated in the laboratory of G. Freeman, clone 339.7G11, final concentration of 69 µg/ml) was performed using the same protocol as above. Slides were then washed in soap water and distilled water for post-IHC staining, dehydrated in graded alcohol and xylene mounted and coverslipped.

C. Case Evaluation

Immunohistochemical stained sections were evaluated by two hematopathologists with concurrence. The intensity of staining of tumor cells for PD-L1 and Gal1 was scored as 0 (n) staining), 1+ (weak or equivocal staining), 2+ (moderate staining), or 3+ (strong staining). The percentage of tumor cell staining was also assessed. A case was considered positive if at least 20% of tumor cells showed 2+ or 3+ staining. Only membranous staining was considered when assessing PD-L1. For JunB and p-cJun staining, a case was considered positive if at least 20% of tumor cells displayed nuclear staining. Macrophages, which are positive for Gal1 and PD-L1, served as internal controls for each case. Appropriate external negative (tonsil) and positive (Hodgkin lymphoma) controls were also included with each experiment.

D. Results

Programmed cell death ligand 1 (PD-L1, also known as B7-H1/CD274) is a cell-surface glycoprotein belonging to the B7 family of costimulatory molecules primarily expressed by antigen-presenting cells and that serve to regulate the cellular immune response (Zou at al. (2008) *Nat. Rev. Immunol*, 8:467-477; Keir et al. (2008) *Annu. Rev. Immunol.* 26:677-704). Binding of PD-L1 to its cognate receptor PD-1 inhibits proliferation of activated T cells in peripheral tissues leading to "T-cell exhaustion," a functional phenotype that can be reversed by PD-1 blockade (Barber et al. (2006) *Nature* 439:682-687: Freeman et al. (2000) *J. Exp Med.* 192:1027-1034; Dong et al. (1999) *Nat. Med.* 5:1365-1369). Many human malignancies, including carcinomas of lung, ovary, and colon; melanomas; anaplastic large cell lymphomas; adult T-cell lymphomas; and cutaneous T-cell lymphomas express PD-L1 whereas normal human tissues, except for monocytes, macrophages, and placental synctiotrophoblasts, do not express detectable levels PD-L1 by immunohistochemistry (Keir et al. (2008) *Annu. Rev. Immunol.* 26:677-704; Doug et al. (2002) *Nat. Med.* 8:793-800 Konishi al. (2004) *Clin. Cancer Res.* 10:5094-5100; Kozako et al. (2009) *Leukemia* 23:375-382; Andorsky et al. (2011) *Clin. Cancer Res.* 17:4232-4244; Kantekure et al. (2012) *Am. J. Dermatopathol.* 34:126-128; Wilcox et al. (2009) *Blood* 114:2149-2158; Wilcox et al. (2012) *Eur. J. Haematol.* 88:465-475). In vitro and preclinical studies have shown that disruption of the PD-1/PD-L1 interaction potentiates the immune response and promotes antitumor activity (Iwai et al. (2002) *Proc. Natl. Acad. USA.* 99:12293-12297). Recent Phase I clinical trials with humanized anti-PD-1 and anti-PD-L1 antibodies have produced durable clinical responses in a subset of patients with solid organ malignancies, most notably melanoma, non-small cell lung carcinoma, and renal-cell carcinoma; suggesting a promising line of therapy based on targeting the PD-1/PD-L1 axis (Brahmer et al. (2010) *J. Clin. Oncol.* 28:3167-3175; Brahmer et al. (2012) *N. Engl. J. Med.* 366:2455-2465; Topalian et al. (2012) *N. Engl. J. Med.* 366:2443-2454).

Gal1 is another immunoregulatory molecule. It has been shown that Gal1 is expressed by a variety of solid tumors and lymphoproliferative disorders, including gastrointestinal malignancies, thyroid papillary carcinoma, laryngeal squamous carcinoma, cutaneous T-cell lymphoma, MLL-rearranged β-lymphoblastic lymphoma, and the Reed-Sternberg cells of classical Hodgkin lymphoma (cHL) (Cedeno-Laurent et al. (2012) *Blood* 119:3534-3538; Juszczynski et al. (2010) *Clin. Cancer. Res.* 16:2122-2130; Saussez al. (2007) *International Journal of Oncology*, 30:1109; Danguy al, (2002) *Biochim. Acta.* 1572:28528-28529; Yamamoto et al. (2008) *Blood* 111:3220-3224; Gandhi et al. (2007) *Blood* 110:1326-1329; Juszezynski et al. (2007) *Proc. Natl. Acad. Sci. USA.* 104:13134-13139; Green et al. (2010) *Blood* 116:3268-3277; Green et al. (2012) *Clin. Cancer Res.* 18:1611-1618; Ouyang et al. (2011) *Blood* 117:4315-4322; Rodig et al. (2008) *Clin Cancer Res.* 14:3338-3344). Gal1 knockdown or blockade with functionally antagonistic antibodies results in tumor rejection in a T-cell dependent manner in pre-clinical models of melanoma and Kaposi sarcoma (KS) (Rabinovich (2005) *Br. J. Cancer.* 92:1188-1192; Rubinstein et al. (2004) *Cancer Cell* 5:241-251; Croci et al. (2012) *J. Exp. Med* 209:1985-2000) and prevents Gal1-mediated apoptosis of CD8+ T cells targeting EBV infected human B-cells in a model of PTLD (Ouyang et al. (2011) *Blood* 117:4315-4322).

The gamma herpes viruses EBV and human herpesvirus 8 (HHV8, also known as Kaposi sarcoma-associated herpesvirus [KSHV]) have the capacity to transform cells and are drivers of a heterogeneous group of aggressive lymphoid and epithelial malignancies with limited treatment options. EBV infects over 90% of healthy individuals and persists in a latent state characterized by the limited expression of viral antigens. Latent EBV infection and periodic viral reactivation are controlled by vigorous, virus-specific host T-cell responses in immunocompetent patients. However, patients who receive immunosuppressive therapy in association with hematopoietic stem cell or solid organ transplantation, rheumatologic conditions, or are otherwise immunocompromised, for instance due to HIV/AIDS, can reactivate the EBV type III latency program and develop malignancies such as PTLD. It has been shown that the majority of EBV+ PTLDs express Gal1 and PD-L1. The expression of these proteins is dependent upon active AP-1 signaling, including JunB and cJun, and which, in turn, is initiated by the viral signaling molecules LMP1 and 2A (Ouyang et al. (2011) *Blood* 117:4315-4322; Green et al. (2012) *Clin. Cancer Res.* 18:1611-1618). Additional immunodeficiency related malignancies include EBV-associated diffuse large B-cell lymphoma (DLBCL), primary effusion lymphoma (PEL), and plasmablastic lymphoma (PBL). EBV infection is also associated with extranodal NK/T cell lymphoma (ENKTCL), nasopharyngeal carcinoma (NPC), and endemic Burkitt lymphoma (BL). Strategies for immune evasion by these tumor types; if any, are largely unknown.

HHV8, unlike EBV, is a gamma herpes virus that infects only a few individuals (5% of healthy individuals) but, similar to EBV, maintains a latent infection that is controlled by the host immune response. In an immunocomprised state, reactivation of the lytic replication program can lead to the development of HHV8-associated malignancies including primary effusion lymphoma (PEL) and KS (Cesarman (2011) *Cancer Lett.* 305:163-174: Taylor et al. (2011) *Cancer Lett.* 305:263-278). As for many EBV+ tumors, it is unknown whether HHV8+ tumors harbor mechanisms for immune escape.

Validation of PD-L1 Antibody for Immunohistochemistry

Figure 5:
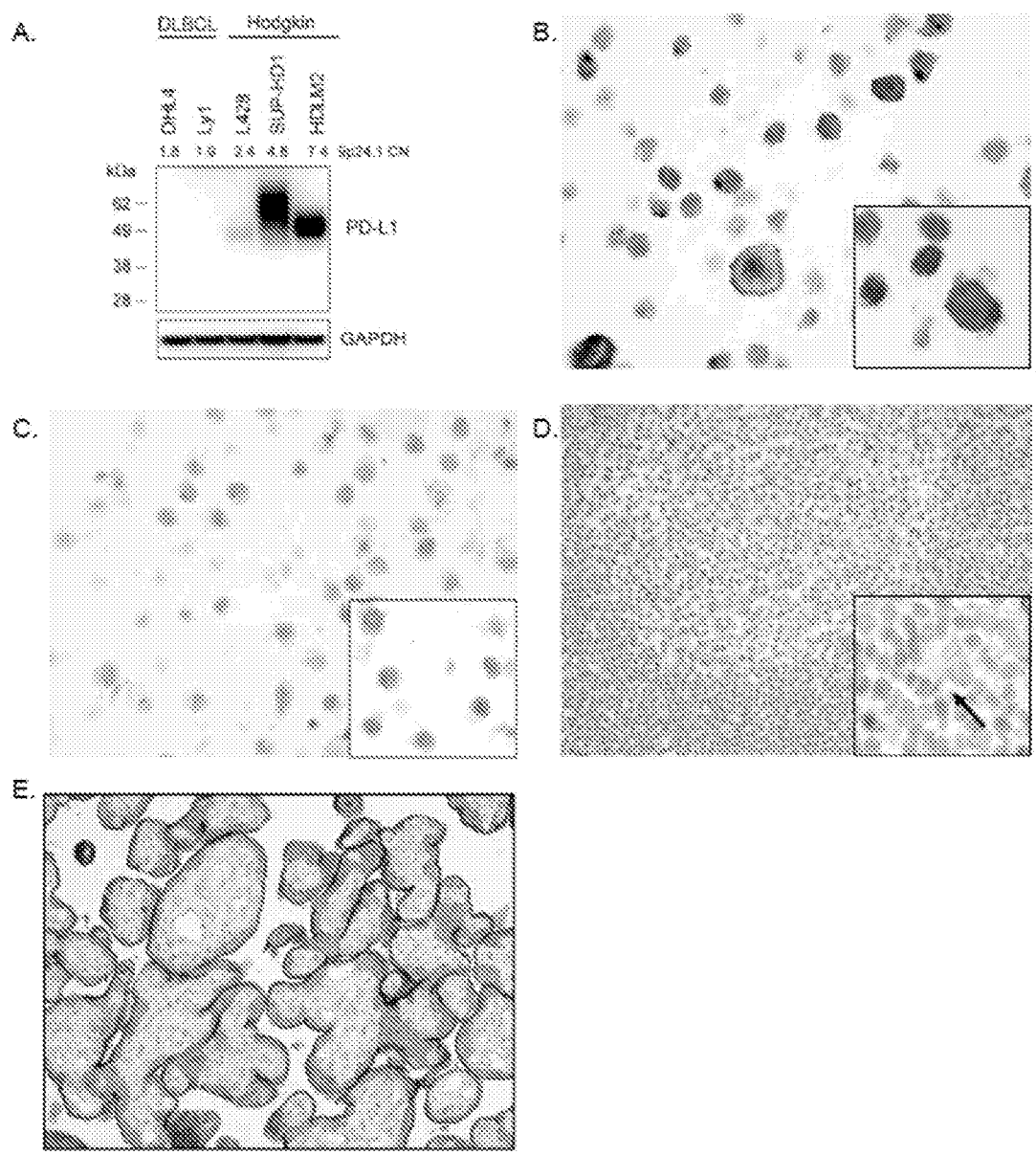
FIGS. 5A-5E show that a rabbit anti-human PD-L1 monoclonal antibody demonstrates both sensitive and specific staining for PD-L1 on a set of well characterized cell lines and tissues.

After testing a variety of commercially available antibodies, a novel rabbit monoclonal antibody demonstrating both sensitive and specific staining for PD-L1 on a set of well characterized cell lines and tissues was identified (FIG. 5). By Western blot analysis, the anti-PD-L1 antibody recognized a protein of 55 kDa, the expected size of PD-L1, in the Hodgkin cell lines; HDLM2 and L428 (FIG. 5A), both of which have been previously shown to express the antigen, but not in the diffuse large B-cell lymphoma (DLBCL) cell lines SU-DHL4 and OCI-Ly1 (FIG. 5A), which have been previously shown to lack PD-L1 (Green et al. (2010) *Blood* 116:3268-3277). Similarly, immunohistochemical (IHC) analysis of formalin fixed paraffin embedded (FFPE) cell lines revealed robust staining of HDLM2 that in a membranous and cytoplasmic pattern (FIG. 5B). In contrast, there was no staining of the FFPE cell line, SU-DHL4 (FIG. 5C). The staining pattern was identical using the mouse monoclonal antibody (FIGS. 5B and 5C insets). Additional IHC analysis of transfected cell lines showed specific staining by both rabbit and mouse PD-L1 antibodies of cell lines expressing human PD-L1 but not human PD-L2. The data indicate that IHC analysis using, both the rabbit and mouse monoclonal antibodies is specific for PD-1 protein.

IHC analysis of human placenta, a tissue known to express PD-L1 at high levels, revealed specific staining of syncitial trophoblasts in accordance with previous results (FIG. 5E; Keir et al. (2008) *Annu. Rev. Immunol.* 26:677-704). In contrast, the lymphocytes of human tonsil, including those in the B-cell rich secondary follicles and the T-cell rich interfollicular regions were largely negatives for staining in a membranous pattern (FIG. 5D). High power examination of tonsilar tissue showed distinct membranous staining of the tonsillar epithelial tissue (FIG. 5D) and weak, membranous staining of scattered cells morphologically consistent with macrophages (FIG. 5D, inset). A modest degree of general, nonspecific background staining was observed in tonsillar tissue depending upon the dilution necessary to achieve optimal final concentration of antibody required for IHC (final concentration 6.2 µg/ml to concentrations ranged from (0.22 to 1.55 mg/ml). Only tumor cell membrane staining was considered positive (FIG. 5).

Expression of PD-L1 in cHL and DLBCL

Augmented PD-L1 transcripts in the Reed-Sternberg (RS) cells of cHL attributable to amplification of 9p24, a genomic region that includes PD-L1 and Jak2, in RS cells, or to EBV infection of RS Cells, has previously been demonstrated (Green et al. (2010) *Blood* 116:3268-3277; Green et al. (2012) *Clin. Cancer Res.* 18:1611-1618). For a subset of cases (19 cases), expression of PD-L1 was examined by IHC using a distinct antibody (Green et (2010) *Blood* 116:3268-3277; Green et al. (2012) *Clin. Cancer Res.* 18:1611-1618).

Figure 6:
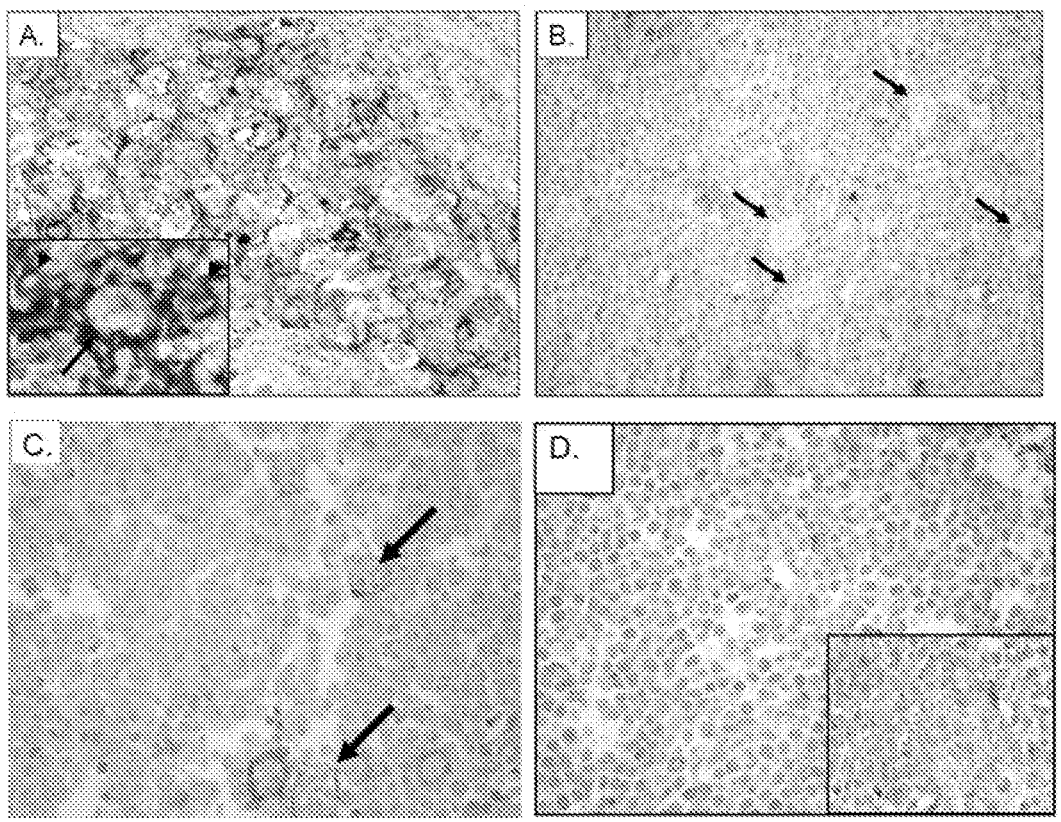
FIGS. 6A-6D show the results of immunohistochemical analyses of PD-L1 in CHL, NLPHL, PMLBCL and TCR-LBCL.

To better determine the incidence of PD-L1 expression in RS cells of cHL, 38 cases of cHL were analyzed using the improved antibody and distinct membranous PD-L1 expression was detected in 33 cases (86.84%). In select cases in which genetic confirmation of amplification of 9p24 was obtained, intense membranous staining for PD-L1 was observed in the vast majority of RS cells (FIG. 6A). However for the majority of cases, genetic information as to the status of 9p24 in the RS cells was not known. PD-L1 expression was seen M cases classified as nodular sclerosis (NS), mixed cellularity (MC), and not other specified (NOS) subtypes-including those both with or without EBV (Table 3). In contrast nodular, lymphocyte predominant Hodgkin lymphoma revealed distinct membranous staining for PD-L1 in only 7% of cases (FIG. 6B; Table 3). In contrast to cHL, the majority (7 of 66 cases, 11%) of diffuse large B-cal lymphoma, not otherwise specified (DLBCL, NOS) was negative for PD-L1 (FIG. 6C). Each case of DLBCL, NOS was confirmed to be negative for EBV, and to have arisen in a patient with no known history of immunosuppression or immunodeficiency.

TABLE 3

Pathological characteristics and PD-L1 expression in Hodgkin lymphomas

| Diagnosis | Case # | EBV status | % malignant cells | % malignant cells positive* | % total tumor cellularity positive** |
|---|---|---|---|---|---|
| NSCHL | 1 | − | 20 | 95 | 80 |
| | 2 | − | 5 | 95 | 70 |
| | 3 | − | 2 | 90 | 70 |
| | 4 | − | 5 | 95 | 60 |
| | 5 | + | 5 | 95 | 50 |
| | 6 | nd | 10 | 90 | 40 |
| | 7 | + | 5 | 90 | 40 |
| | 8 | + | 5 | 50 | 40 |
| | 9 | − | 2 | 95 | 40 |
| | 10 | − | 10 | 95 | 30 |
| | 11 | − | 10 | 95 | 30 |
| | 12 | + | 2 | 95 | 30 |
| | 13 | nd | 2 | 0 | 30 |
| | 14 | − | 10 | 95 | 20 |
| | 15 | − | 10 | 95 | 20 |
| | 16 | + | 5 | 95 | 20 |
| | 17 | nd | 5 | 95 | 20 |
| | 18 | − | 5 | 90 | 20 |
| | 19 | + | 2 | 90 (1+/M)*** | 20 |
| | 20 | + | 5 | 95 | 10 |
| | 21 | − | 5 | 90 | 10 |
| | 22 | − | 2 | 90 (2+/C)*** | 10 |
| | 23 | − | 2 | 80 | 10 |
| | 24 | nd | 5 | 10 | 5 |
| | 25 | − | 2 | 20 (1+/C)*** | 2 |
| MCCHL | 1 | + | 2 | 95 | 80 |
| | 2 | + | 10 | 90 | 70 |
| | 3 | − | 10 | 80 | 70 |
| | 4 | + | 2 | 90 | 70 |
| | 5 | − | 2 | 95 | 60 |
| | 6 | + | 2 | 90 | 40 |
| | 7 | − | 2 | 70 | 20 |
| | 8 | − | 2 | 90 (1+/C)*** | 10 |
| CHL-NOS | 1 | − | 90 | 90 | 90 |
| | 2 | − | 90 | 90 | 90 |
| | 3 | − | 50 | 90 | 90 |
| | 4 | − | 10 | 50 | 80 |
| | 5 | + | 2 | 95 | 60 |
| NLPHL | 1 | − | 5 | 2 | 20 |
| | 2 | nd | 2 | 20 (1+/M)*** | 10 |
| | 3 | − | 2 | 5 | 10 |
| | 4 | nd | 2 | 5 | 10 |
| | 5 | nd | 2 | 0 | 10 |
| | 6 | − | 2 | 0 | 10 |
| | 7 | − | 2 | 0 | 10 |
| | 8 | nd | 2 | 0 | 10 |
| | 9 | nd | 2 | 0 | 5 |
| | 10 | nd | 2 | 0 | 5 |
| | 11 | nd | 2 | 0 | 5 |
| | 12 | nd | 2 | 0 | 5 |
| | 13 | − | 2 | 0 | 5 |
| | 14 | − | 2 | 0 | 5 |
| | 15 | − | 2 | 0 | 5 |

*≥ membranous staining;
**≥2+ membranous staining and/or cytoplasmic staining;
***≥ scored as negative;
NSCHL—nodular sclerosis classical Hodgkin lymphoma (CHL);
MCCHL—mixed cellularity CHL;
NOS—not otherwise specified;
NLPHL—nodular lymphocyte predominant Hodgkin lymphoma.

Expression of PD-L1 and Gal1 in EBV- and HHV8-Positive Tumors.

The results of immunohistochemical staining for PD-L1, Gal1, JunB, and p-cJun in EBV- and HHV8-positive tumors are summarized in Table 4. Strong membranous staining for PD-L1 was observed for all EBV-positive DLBCL of the elderly (5/5, 100%) and EBV-positive immunodeficiency-related DLBCL (6/6, 100%). In contrast, no cases of EBV-positive BL (0/7, 0%) were positive for PD-L1 in either the tumor cells or the intermixed, tumor-associated macrophages (FIG. 6D).

Figure 7:
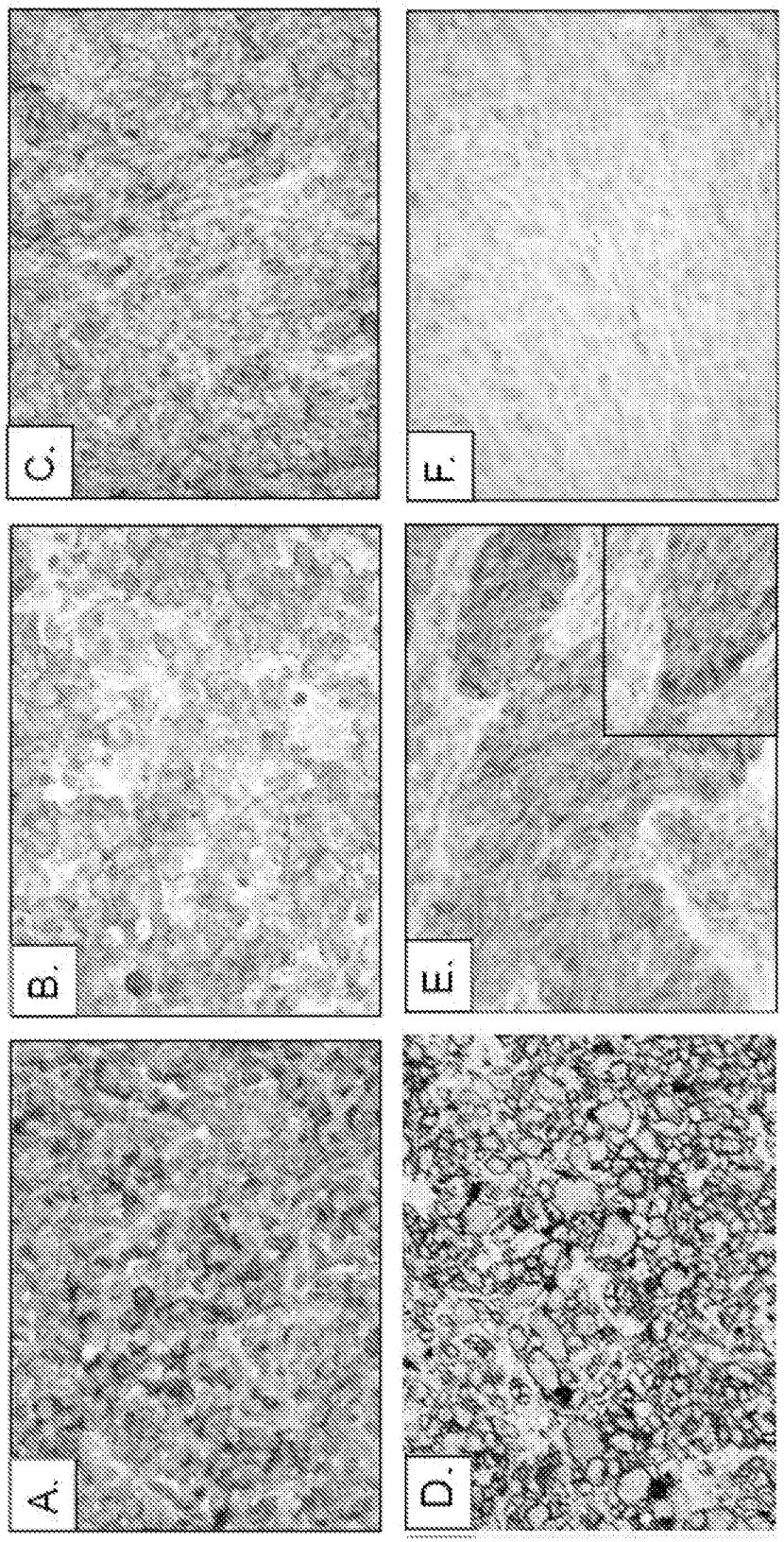
FIGS. 7A-7F show the results of immunohistochemical analyses of PD-L1 expression in viral-associated lymphomas and additional cancers. Representative cases of EBV-positive plasmablastic lymphoma (PBL) (FIG. 7A), HHV8-positive primary effusion lymphoma (PEL) (FIG. 7B), EBV-positive extranodal NK/T-cell lymphoma (ENKTCL) (FIG. 7C), EBV-negative post-transplant lymphoproliferative disease (PTLD) (FIG. 7D), EBV-positive nasopharyngeal carcinoma (NPC) (FIG. 7E), and HHV8-positive Kaposi sarcoma (KS) (FIG. 7F) stained with rabbit anti-PD-L1 or mouse anti-PD-L1 (insets).

The majority of tumor cells in all cases of ENKTCL (6/6, 100%) (FIG. 7C and Table 4) and NPC (9/9, 100%) (FIG. 7E and Table 4) showed staining for PD-L1. Two of 7 (29%) cases of PBL (FIG. 7A and Table 4) and 1 of 3 (33%) cases of PEL (FIG. 7B and Table 4) were positive for PD-L1. Three of 7 (43%) cases of EBV-negative PTLD showed strong, membranous staining for PD-L1 and an additional 3 cases showed cytoplasmic PD-L1 staining (FIG. 7D and Table 4). No cases of KS (0/9, 0%) showed membranous PD-L1 staining (FIG. 7F). One case of KS showed cytoplasmic staining for PD-L1 (Table 4).

Figure 8:
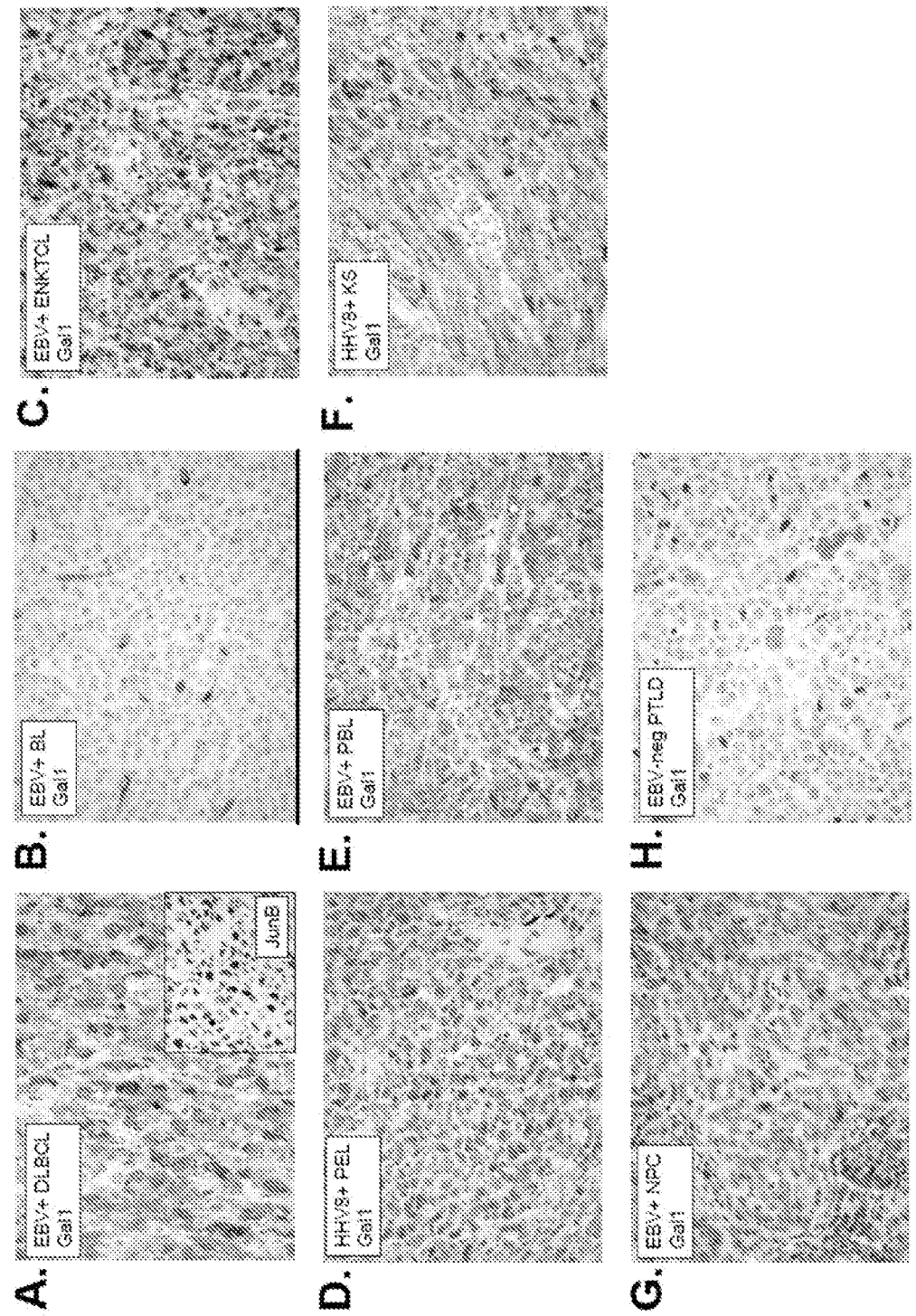
FIGS. 8A-8H show the results of immunohistochemical analyses of Gal1 expression in viral-associated lymphomas and additional cancers. Representative cases of EBV-positive diffuse large B-cell lymphoma (DLBCL) (FIG. 8A). EBV-positive Burkitt lymphoma (BL) (FIG. 8B), EBV-positive extranodal NK/T-cell lymphoma (ENKTCL) (FIG. 8C), HHV8-positive primary effusion lymphoma (PEL) (FIG. 8D), EBV-positive plasmablastic lymphoma (PBL) (FIG. 8E), HHV8-positive Kaposi sarcoma (KS) (FIG. 8F), EBV-positive nasopharyngeal carcinoma (NPC) (FIG. 8G), and EBV-negative post-transplant lymphoproliferative disease (PTLD) (FIG. 8H).

The majority of EBV-positive DLBCL of the elderly (5/8, 63%) (FIG. 8), EBV-positive immunodeficiency-related DLBCL (6/8, 75%) (Table 4) were positive for Gal1. When positive, Gal1 was typically diffusely positive in a cytoplasmic staining pattern among the majority of tumor cells (FIG. 8A). In contrast, no cases of EBV-positive BL were positive for Gal1 (Table 4 and FIG. 8B), ENKTCL (8/10, 80%), PEL (4/4, 100%), PBL (8/11, 73%), and KS (7/9, 78%) cases showed strong Gal1 staining (FIGS. 8C-6F and Table 4). No cases of NPC (0/9, 0%), or EBV-negative PTLD (0/8, 0%) showed expression of Gal1 by immunohistochemistry (FIGS. 8G-8H and Table 4).

Expression of JunB, and p-cJun in EBV- and HHV8-Positive Tumors.

It has previously been shown that EBV-encoded proteins promote PD-L1 and Gal1 expression in tumor cells via AP-1 signaling (Green et al. (2012) *Clin. Cancer Res.* 18:1611-1618). Thus, the cohort of virus-associated tumors was analyzed for expression and nuclear localization of the AP-1 transcription factors JunB and phospho (active)-c-Jun. All classes of EBV- and HHV8-positive tumors examined in this study exhibited nuclear staining for JunB and p-c-Jun in at least 50% of cases, with the exception of BL cases of which only one case showed expression of p-cJun (Table 4).

whereas two cases were positive for only JunB. One case was negative for PD-L1 but showed positive staining for JunB and p-cJun.

Cases of EBV-positive DLBCL of the elderly and EBV-positive immunodeficiency-related DLBCL that showed negative Gal1 staining were positive for JunB and p-cJun staining. One ease of ENKTCL, which was negative for EBER, was negative for Gal1, JunB and p-cJun but was positive for PD-L1. A second case of ENKTCL that was negative for Gal1 was positive for JunB, p-cJun, and PD-L1.

Three cases of NPC, which were negative for Gal1 but positive for PD-1, were positive for JunB but scored negative for p-cJun. The case of KS that showed cytoplasmic staining for PD-L1 was positive for both JunB and p-cJun.

E. Discussion

Multimodal and combinatorial approaches to cancer therapy are increasingly targeting multiple mechanisms involved in tumor pathogenesis. Immune evasion is an emerging hallmark of cancer that presents an attractive target with several recent advances, including clinical trials with humanized antibodies directed against immune checkpoint molecules such as CTLA4 and PD-1 (Hanahan et al. (2011) *Cell* 144:646-674 and Pardoll (2012) *Nat. Rev. Cancer* 12:252-264). Recent Phase I clinical trials with anti-PD-1 and anti-PD-L1 antibodies in patients with solid tumors demonstrate the need for a reliable method of identifying those tumors that express high levels of PD-L1 in order to improve treatment efficacy (Brahmer et al. (2010) *J. Clin. Oncol.* 28:3167-3175; Brahmer et al. (2012) *N. Engl. J. Med.* 366:2455-2465; and Topalian et al. (2012) *N. Engl. J. Med.* 366:2443-2454). In the trial with anti-PD-1, 9 of 25 cases that expressed any detectable tumor-associated PD-L1 by immunohistochemistry showed a durable clinical response, whereas no clinical effect was observed in those patients with tumors lacking detectable PD-L1 (Topalian et

TABLE 4

PD-L1, Gal1, JunB and p-cJun expression in EBV- and HHV-8-positive tumors

| Diagnosis | PD-L1 | | | Gal1 | | JunB | | p-cJun | |
|---|---|---|---|---|---|---|---|---|---|
| | | % pos | | | | | | | |
| | n | membr (n) | % cyto (n) | n | % pos (n) | n | % pos (n) | n | % pos (n) |
| EBV+ DLBCL elderly | 5 | 100 (5) | | 8 | 63 (5) | 6 | 100 (6) | 6 | 100 (6) |
| EBV+ DLBCL immunodef | 6 | 100 (6) | | 8 | 75 (6) | 8 | 100 (8) | 6 | 100 (6) |
| Combined | 11 | 100 (11) | | 16 | 68 (11) | 14 | 100 (14) | 12 | 100 (12) |
| Extranodal NK/T | 6 | 100 (6) | | 10 | 80 (8) | 7 | 86 (6) | 6 | 83 (5) |
| Plasmablastic lymphoma | 7 | 29 (2) | | 11 | 73 (8) | 7 | 71 (5) | 7 | 86 (8) |
| EBV+ Burkitt | 7 | | | 10 | 0 (0) | 9 | 0 (0) | 9 | 11 (1) |
| Nasopharyngeal carcinoma | 9 | 100 (9) | | 9 | 0 (0) | 9 | 100 (9) | 9 | 67 (8) |
| EBV- negative PTLD | 7 | 43 (3) | 43 (3) | 8 | 0 (0) | 8 | 88 (7) | 6 | 50 (4) |
| Kaposi sarcoma | 9 | | 7 (1) | 9 | 78 (7) | 9 | 100 (9) | 9 | 89 (8) |
| Primary effusion lymphoma | 3 | 33 (1) | | 4 | 100 (4) | 3 | 100 (3) | 3 | 100 (3) |

For PBL, of the five cases that were negative for PD-L1, two were also negative for Gal1, JunB and p-cJun staining. One PBL case that was negative for all four markers was also negative for EBER.

In contrast, the two cases of PEL that were negative for PD-L1 showed positive staining for Gal1, JunB and p-cJun.

For EBV-negative PTLD, which were all negative for Gal1, of the three cases that showed strong membranous staining for PD-1, two cases were positive for both JunB and p-cJun and one case was negative for p-cJun but positive for JunB. Of the three cases that showed cytoplasmic staining for PD-L1, one case was positive for both JunB and p-cJun al. (2012) *N. Engl. J. Med.* 366:2443-2454). The data described herein demonstrates robust membranous PD-L1 staining in the majority of EBV-positive DLBCL of the elderly and immunocompromised, NPC, and ENKTCL cases. A minority of EBV-negative PTLD, EBV-negative DLBCL, PBL, and PEL cases were positive for PD-L1.

Gal1 is also an emerging immunomodulatory molecule that leads to apoptosis of T cells and blockade of Gal1 gene expression promotes tumor rejection in mouse models (Liu et al. (2005) *Nat. Rev. Cancer* 5:29-41 and Rubinstein et al. (2004) *Cancer Cell* 5:241-251). Gal1 staining has been determined herein to be found in the majority of EBV-positive DLBCL, ENKTCL, and PBL, as well as the HHV8- associated tumors KS and PEL. These data indicate that classes of virally-driven malignancies can benefit from targeted therapy against PD-L1 and Gal1 and provide a reliable method for identifying those cases that may specifically respond to such treatment.

In line with previous studies examining the AP-1 and EMV-dependent expression of PD-L1 and Gal1 in EBV-positive PTLD and cHL (Juszczynski et al. (2007) *Proc. Natl. Acad. Sci. USA.* 104:13134-13139, Green et al. (2012) *Clin. Cancer Res.* 18:1611-1618, Ouyang et al. (2011) *Blood* 117:4315-4322, Rodig et al. (2008) *Clin. Cancer Res.* 14:3338-3344); Gal1 and PD-L1 expression correlated with expression of p-cJun and JunB in EBV-positive DLBCL and ENKTCL. Most EBV-negative PTLD cases showed expression of JunB and p-cJun, despite being negative for EBV by previous EBER analysis, and a subset of these cases showed membranous PD-L1 staining. Some of these cases also showed cytoplasmic PD-L1 staining, which is of uncertain significance as it is likely that only membrane expression of PD-L1 would contribute to tumor immune evasion. These tumors were also uniformly negative for Gal1, in contrast to EBV-positive PTLD (Ouyang et al. (2011) *Blood* 117:4315-4322). Similarly, the majority of NPC cases had activated AP-1 signaling and strong PD-L1 staining but were negative for Gal1. For PBL and PEL, expression of the AP-1 components correlated well with Gal1 expression, but several cases were negative for PD-L1. Together, these data indicate alternative mechanisms fix the upregulation of PD-L1 and Gal1 and that AP-1 activation or EBV-positivity is not sufficient for driving expression of Gal1.

Amplification of the 9p24 locus, as shown for cHL (Green et al. (2010) *Blood* 116:3268-3277), may be a common finding in tumors that overexpress PD-L1 but are negative for EBV or activated AP-1 components. Conversely, interrogation of tumors that harbor 9p24 amplification, such as gray zone lymphoma and breast carcinoma (Eberle et al. (2011) *Modern Pathology* 24:1586-1597 and Wu et al. (2012) *Oncogene* 31:333-341), for PD-L1 expression would further identify candidates for anti-PD-L1 immunotherapy. Alternatively, aberrant signaling through the STAT3 pathway, first demonstrated in ALK-positive T-cell lymphoma as a result of the NPM/ALK fusion protein (Marzee et al. (2008) *Proc. Natl. Acad. Sci USA.* 105:20852-2(857) can provide another mechanism for PD-L1 expression.

An interesting exception to the other EBV-positive malignancies was the absence of Gal1, PD-L1, and JunB/cJun staining in virtually all EBV-positive BL cases. It is known that the EBV latency program in BL is different from DLBCL (Vereide et al. (2011) *Blood* 117:1977-1985 and Bornkamm (2009) *Semin. Cancer. Biol.* 19:351-365). Specifically, a smaller set of viral proteins are expressed in BL and LMP1 is not expressed. In studies of EBV-dependent expression of Gal1 and PD-L1 in PTLD and cHL, it was shown that Gal1 and PD-1 expression was dependent specifically on LMP1 (Green et al. (2012) *Clin. Cancer Res.* 18:1611-1618 and Ouyang et al. (2011) *Blood* 117:4315-4322). Thus, lack of LMP1 in BL tumor cells may result in the failure to activate AP-1 signaling and consequently an absence of detectable Gal1 and PD-L1 expression. Furthermore, it has been shown that the Myc protein counteracts the expression of PD-L1 (Durand-Panteix et al. (2012) *J. Immunol.* 189:181-190). Thus it is believed that BL tumor cells, by virtue of myc translocation/amplification and an altered EBV latency program, would not benefit from targeted therapy against Gal1 or PD-L1. This finding also raises the possibility of downregulation of PD-L1 in other tumors that overexpress Myc, such as so-called double hit DLBCL (Aukema at al. (2011) *Blood* 117:2319-2331).

For the HHV8-positive malignancies KS and PEL, the majority of cases were positive for Gal1 and AP-1 components, but only one case of PEL showed membranous PD-L1 staining and only one case of KS showed cytoplasmic PD-L1 staining. Endothelial cells also stain for Gal1 requiring careful interpretation of KS, which represents a proliferation of endothelial-derived tumor cells. A recent analysis of Gal1 expression in KS included analysis of benign vascular proliferations and Gal1 was only upregulated in KS samples (Croci et al. (2012) *J. Exp. Med.* 209:1985-2000). Furthermore, the same neutralizing anti-Gal1 antibody used in our previous studies was shown to attenuate abnormal angiogenesis and promote tumor regression in mouse models of KS (Croci et al. (2012) *J. Exp. Med.* 209:1985-2000).

Correlation of PD-L1 expression in human tumors with prognosis has so far resulted in conflicting results, perhaps due to inconsistent immunohistochemical protocols and other technical reasons (Hino et al. (2010) *Cancer* 116:1757-1766, Gadiot et al. (2011) *Cancer* 117:2192-2201, Hamanishi et al. (2007) *PNAS* 104:3360-3365, Thompson of al. (2004) *PNAS* 101:17174-17179, Thompson et al. (2006) *Cancer Res.* 66:3381-3385, Wu et al. (2006) *Acta Histochemica.* 108:19-24, Ghebeh at al. (2006) *Neoplasia* (New York, N.Y.) 8:190, Gao et al. (2009) *Clin. Cancer Res.* 15:971-979, and Nomi et: at (2007) *Clin. Cancer Res.* 13:2151-2157). A robust staining protocol has been described herein that can be easily replicated by automated staining machines commonly used in clinical practice. The studies described herein used a fairly high threshold for positive staining (at least 20% tumor cells exhibiting strong membranous staining) whereas prior studies have accepted lower levels of PD-L1 expression (Topalian et al. (2012) *N. Engl. J. Med.* 366:2443-2454).

Macrophages have been previously observed to express PD-L1 and Gal1, probably as a consequence of normal immune modulation. In the studies described herein, macrophages provided a consistent internal positive control for both PD-L1 and Gal1 staining. In some cases, careful examination of cell morphology was required to determine staining on tumor cells, particularly in cases with abundant: macrophages. For PD-L1, marked staining heterogeneity was noted for some cases of EBV-positive DLBCL, perhaps highlighting tumor heterogeneity. It seems likely that tumors with heterogeneous expression of immune modulating molecules may still be amenable to targeted therapy as blockade of these signals may result in the return of effective immune surveillance that would target the entire tumor.

The EBV and HHV8-driven malignancies are rare but aggressive, often life-threatening neoplasms with limited treatment options, identification of additional classes of tumors and methods to detect specific cases that may be amenable to targeted therapy will lead to more efficient and effective immunotherapy.

Figure 9:
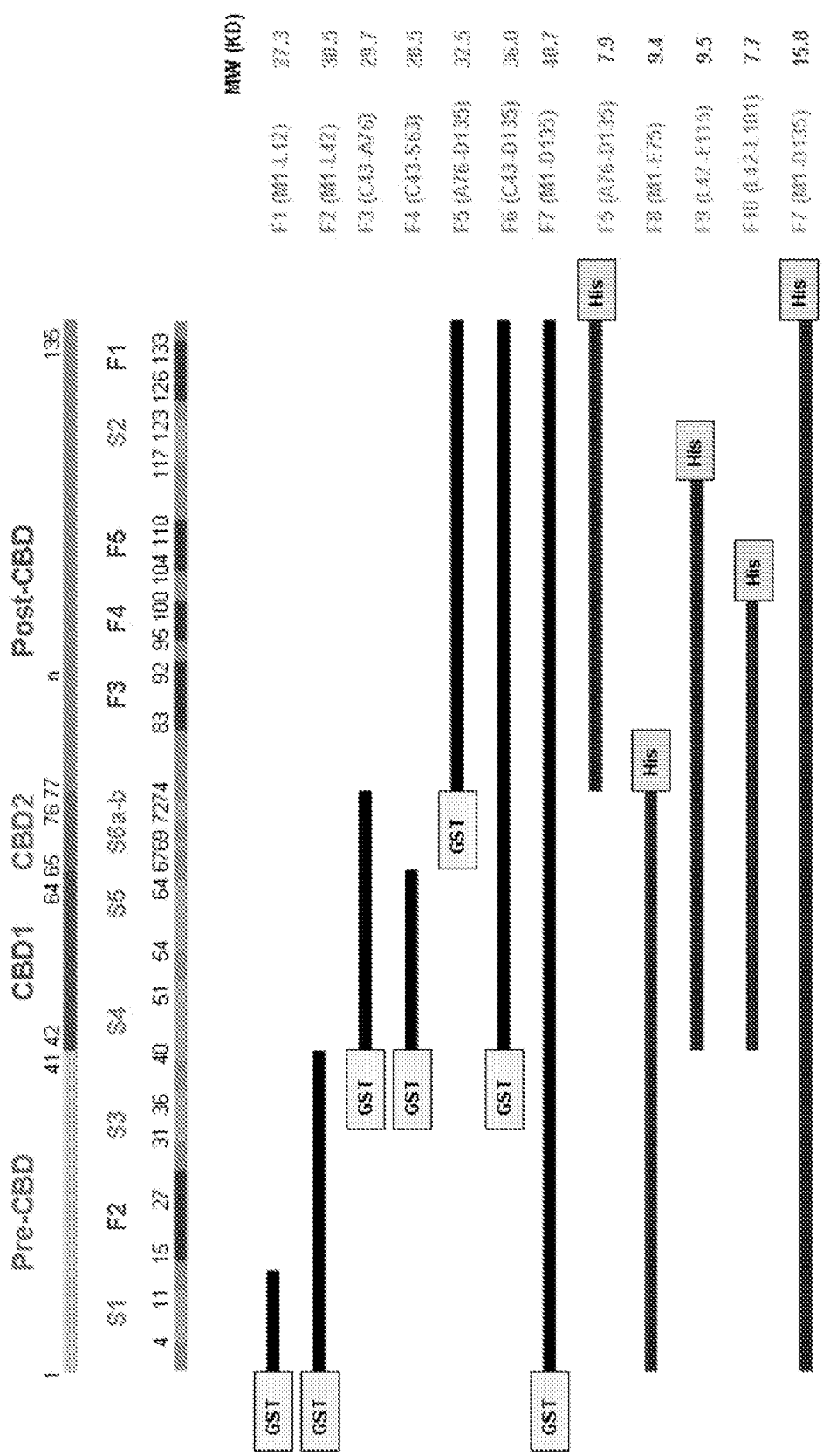
FIG. 9 shows a schematic diagram of recombinant GST-tagged or HIS-tagged human Gal1 (hGal1) and fragments.
Figure 10:
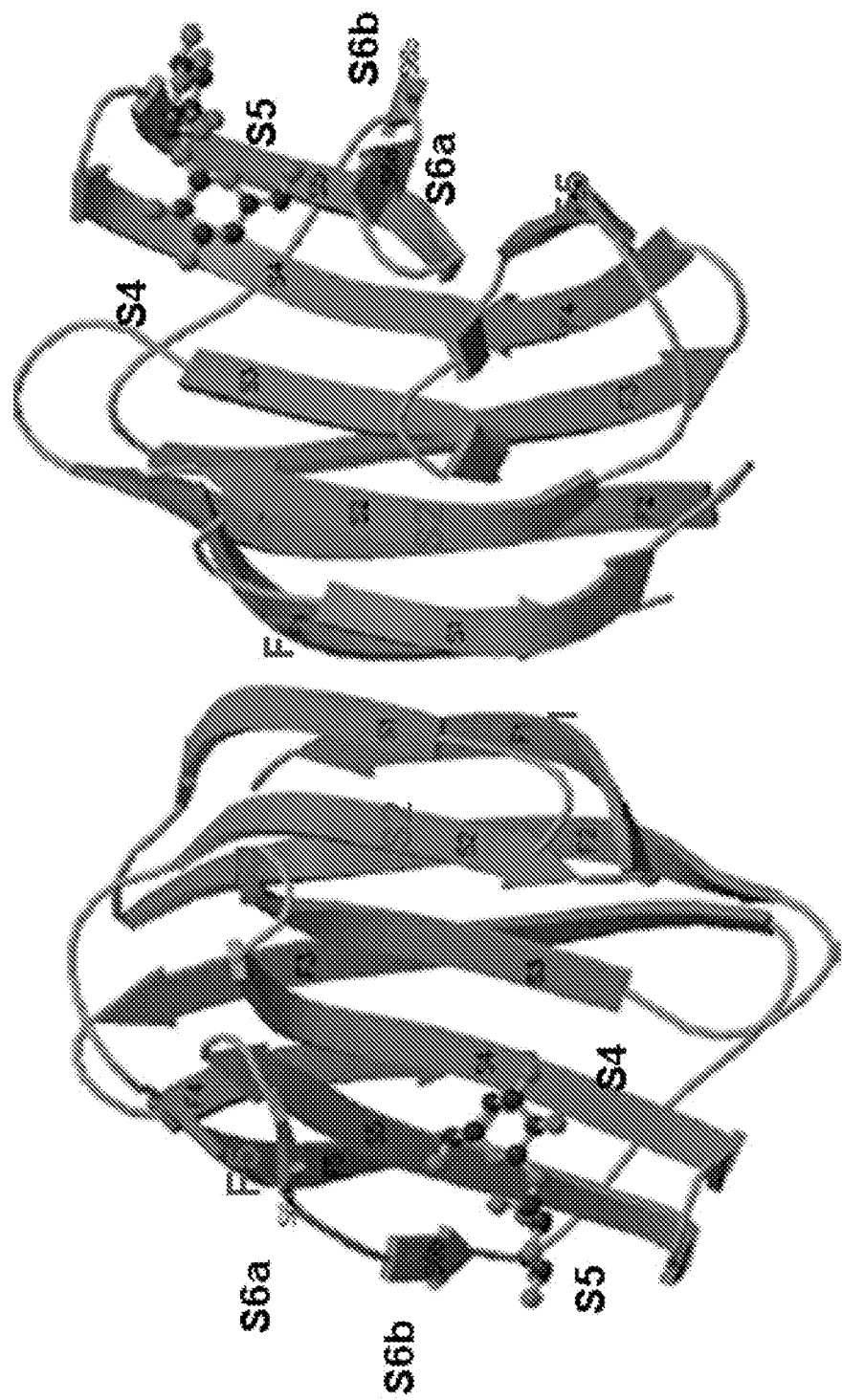
FIG. 10 shows a ribbon diagram of the homodimeric hGal1 with two lactose molecules prepared with MOLSCRIPT. The β-strands in the five-stranded (F1-F5) and six stranded (S1-S6a/S6b) β-sheets are indicated by the letter-number code. The figure was adapted from Lopez-Lucendo et al. (2004) *J. Mol. Biol.* 343:957-970.
Figure 11:
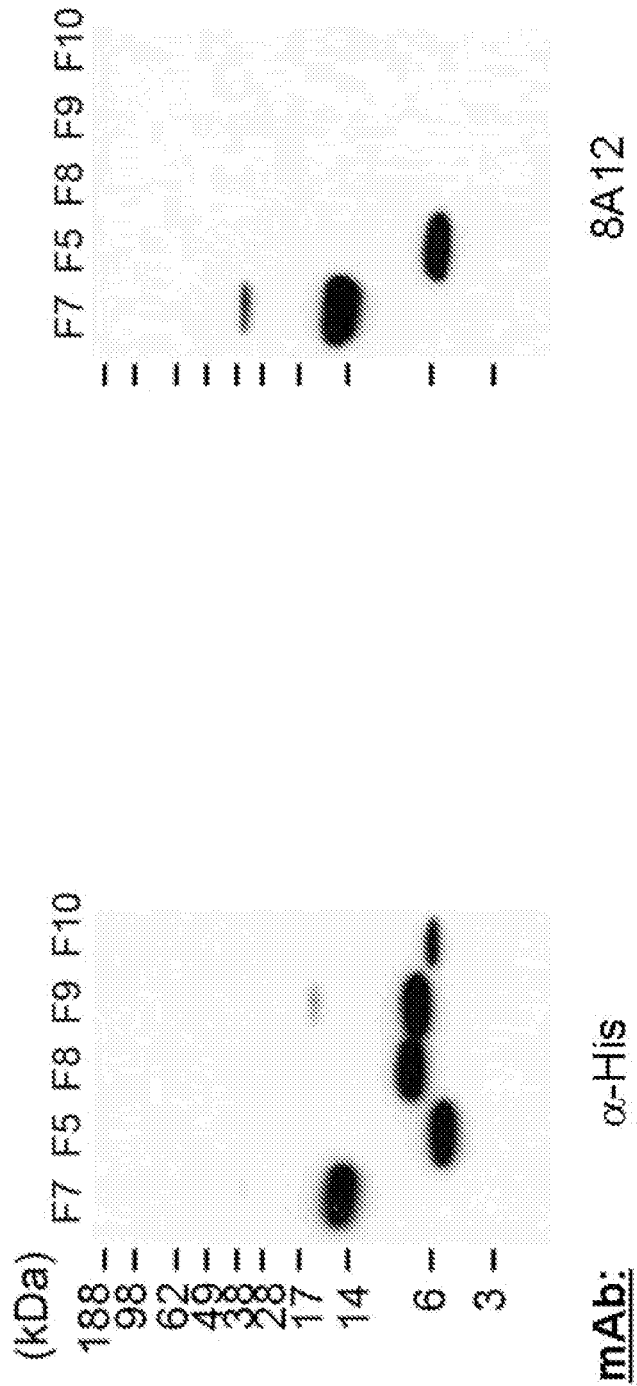
FIG. 11 shows the results of fine epitope mapping for the 8A12 mAb.
Figure 12:
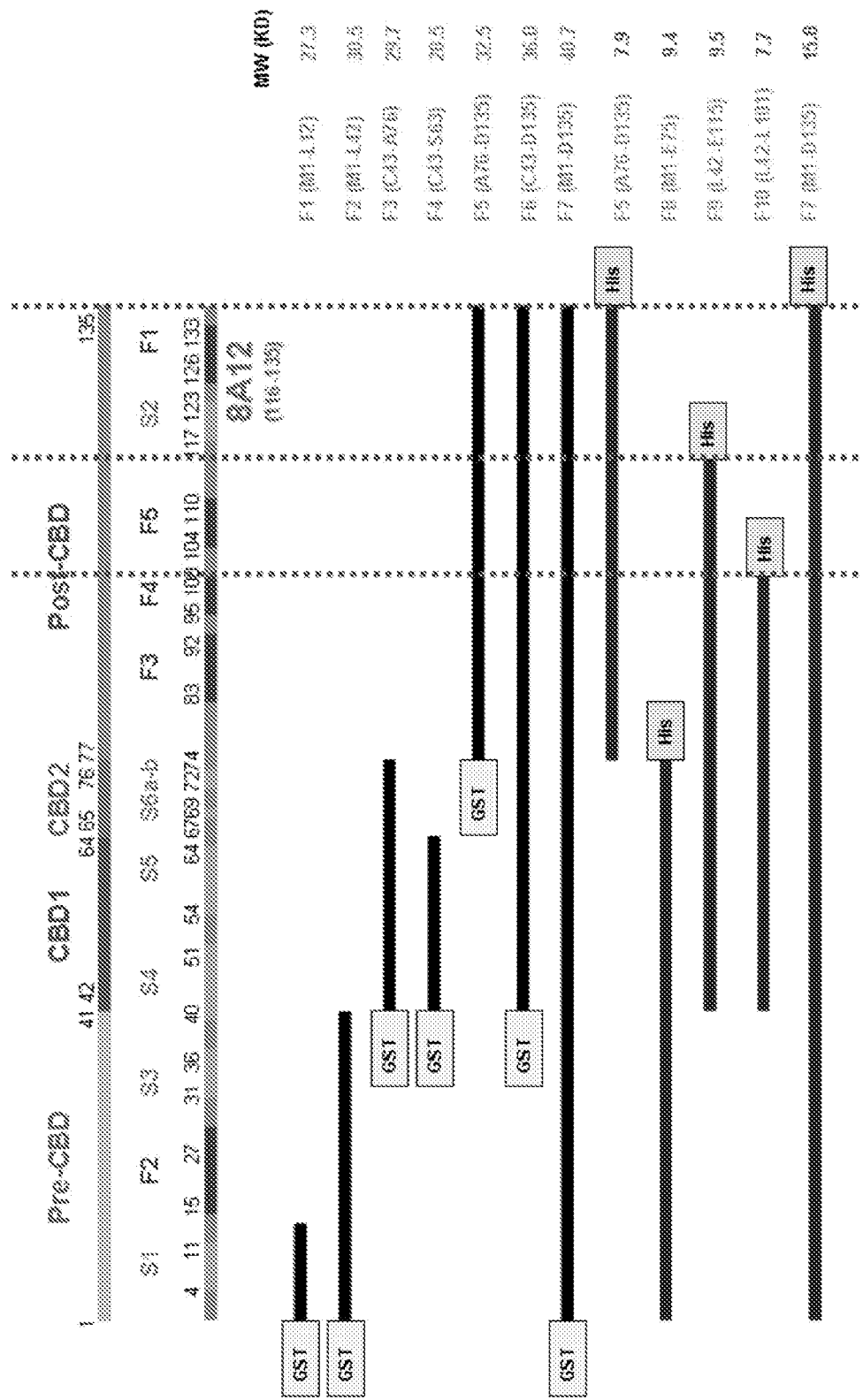
FIG. 12 shows a schematic diagram summarizing the fine epitope mapping results for the 8A12 mAb.

Example 4: Fine Epitope Mapping and Kinetic Analyses of the Anti-Gal1, Non-Neutralizing 8A12 mAb The 8A12 mAb determined to cross-react well with both human Gal1 and mouse Gal1 in FIG. 1 and recognize a post-CBD domain of Gal1 in FIG. 2 was further subjected to fine epitope mapping analyses. In addition to the seven GST-tagged human Gal1 constructs shown in FIG. 3 and produced in *E. coli*, five additional 6×HIS-tagged human Gal1 constructs spanning various portions of the human Gal1 polypeptide were generated in *E. coli* for use in epitope mapping analyses (FIG. 9). FIG. 9 floater demonstrates how the amino acids encompassed by each GST-tagged and HIS-tagged construct maps with respect to the β-strands in the five-stranded β-sheets (F1-F5) and six-stranded β-sheets (S1-S6a/S6b) of the folded human Gal-1 polypeptide (FIG. 10). The anti-Gal1, non-neutralizing 8A12 mAb was determined to recognize recombinant HIS-F7 and HIS-F5 by Western blot analysis (FIG. 11). These results indicate that the 8A12 mAb binds Gal1 within amino acid residues 116-135 (FIG. 12). In addition, such fine epitope mapping data define a structural basis for Gal1 neutralization because the non-neutralizing 8A12 mAb binds to β-sheets S2/F1, which is spatially far away from the carbohydrate binding domain.

Figure 13:
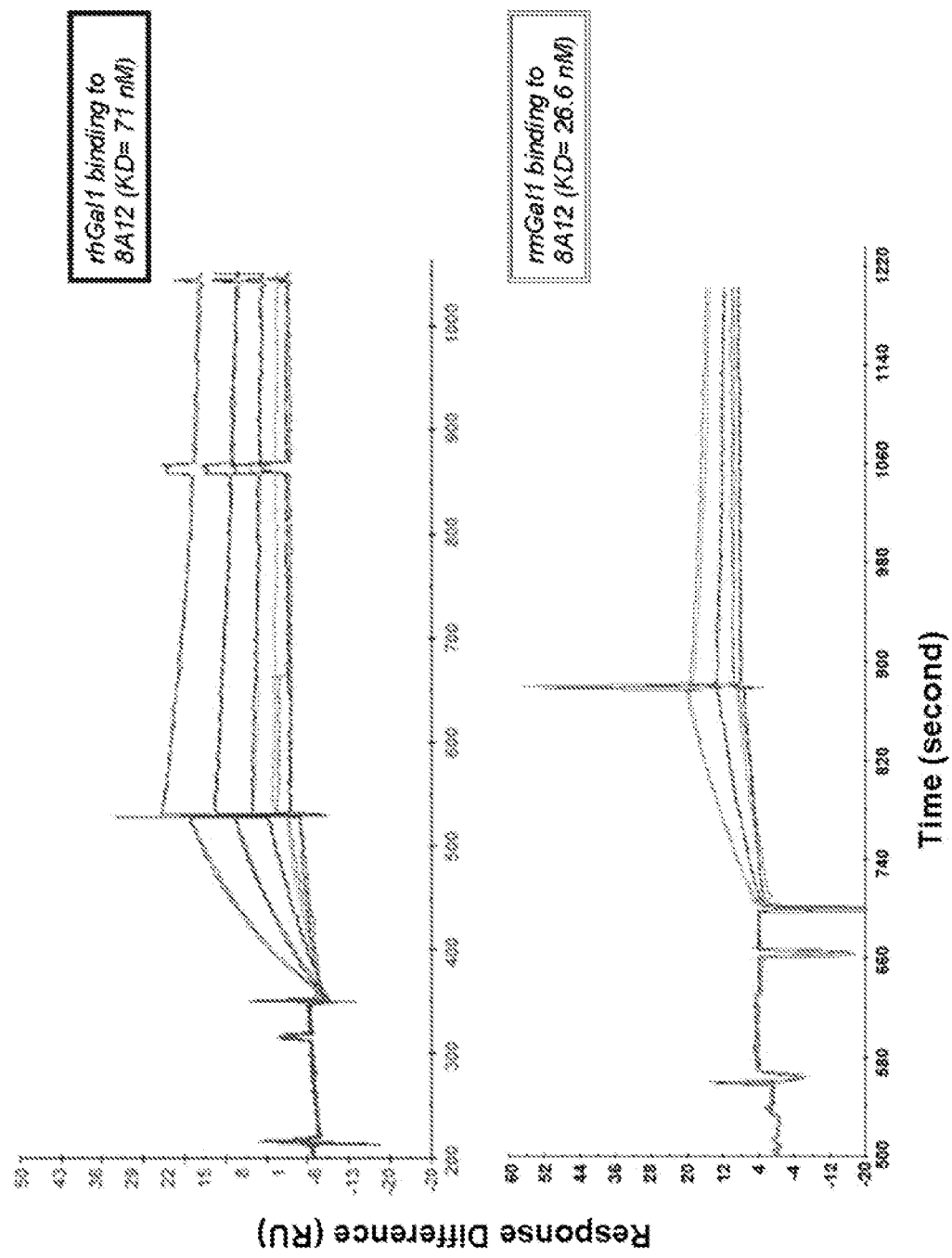
FIG. 13 shows the results of BIAcore analyses for the 8A12 mAb.

Surface Plasmon Resonance (SPR) analyses (also called Biomolecular Interaction Analysis, BIAcore) were also conducted in order to further define the biophysical properties (e.g., $k_{on}$, $k_{off}$, $k_{off}/k_{on}$ ($K_D$) of Gal1's interaction with the 8A12 mAb. SPR experiments were performed at 25° C. in the standard BIAcore running buffer HBS-EP on a BIAcore 3000 Instrument (BIAcore). In brief, anti-mouse antibody was first captured on the CM-5 sensor chip ((GE HealthCare). Afterwards, approximately 250 response units (RU) of anti-Gal1 mAb 8A12 were immobilized (with exception of ~350 RU for rmGal1 assay) and followed by various dilutions of recombinant galectin (human galetin-1, 2, 3, 4, 7, 8, 9 or murine galectin-1 (mGal1), from R&D Systems) to assess the binding of galectin 8A12. All data are shown after subtraction from a channel loaded with buffer alone. Data analysis to obtain the binding curves shown and equilibrium dissociation constant (KD) was performed using BIAevaluation 3.1 (BIAcore) by globally fitting the data to a simple 1:1 (Langmuir) binding model. The 8A12 mAb also showed nM levels of affinity with both rhGal1 and rmGal1 (FIG. 13). In addition, the 8A12 mAb showed no binding or non-specific binding to higher concentrations of other recombinant galectins, including Gal2, Gal3, Gal4, Gal7, Gal8, and Gal9.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A monoclonal antibody, or antigen-binding fragment thereof, that binds galectin-1 (Gal1) wherein the monoclonal antibody comprises:
 a) a heavy chain sequence comprising a CDR-H1, a CDR-H2, and a CDR-H3 sequences, wherein the CDR-H1 sequence consists of an amino acid sequence of RYNMH (SEQ ID NO: 23), the CDR-H2 sequence consists of an amino acid sequence of RIYPGNGDT-SYNQKFKG (SEQ ID NO: 26), and the CDR-H3 sequence consists of an amino acid sequence of WDY (amino acid residues 118-120 of SEQ ID NO: 7); and
 b) a light chain sequence comprising a CDR-L1, a CDR-L2, and a CDR-L3 sequences, wherein the CDR-L1 sequence consists of an amino acid sequence of KSSQSLLDSDGKTYLN (SEQ ID NO: 12), the CDR-L2 sequence consists of an amino acid sequence of LLSKLDS (SEQ ID NO: 15), and the CDR-L3 sequence consists of an amino acid sequence of WQGTHFPYT (SEQ ID NO: 18).

2. The monoclonal antibody, or antigen-binding fragment thereof, of claim 1, wherein the monoclonal antibody or antigen-binding fragment thereof:
 a) is chimeric, humanized, composite, murine, or murine;
 b) is detectably labeled, comprises an effector domain, comprises an Fc domain, and/or is selected from the group consisting of Fv, Fav, F(ab')2, Fab', dsFv, scFv, sc(Fv)2, and diabodies fragments;
 c) inhibits the binding of commercial antibody to Gal1; or
 d) is obtainable from hybridoma 8A12.H9.H10 deposited under deposit accession number PTA-120449.

3. An immunoglobulin heavy and light chain of claim 1.

4. A device or kit comprising the monoclonal antibody or antigen-binding fragment thereof, according to claim 1, said device or kit optionally comprising a label to detect the monoclonal antibody or antigen-binding fragment thereof, or a complex comprising the monoclonal antibody or antigen-binding fragment thereof.

5. An isolated nucleic acid molecule that encodes the light chain, and heavy chain of the monoclonal antibody or antigen-binding fragment of claim 1.

6. A vector comprising the isolated nucleic acid of claim 5.

7. A host cell which comprises the isolated nucleic acid of claim 5, comprises the vector of claim 6, expresses the antibody or antigen-binding fragment thereof of claim 1, or is accessible under deposit accession number PTA-120449.

8. A method of producing the antibody according to claim 1, which method comprises the steps of: (i) culturing a transformed host cell which has been transformed by a nucleic acid comprising a sequence encoding the monoclonal antibody according to claim 1 under conditions suitable to allow expression of said antibody; and (ii) recovering the expressed antibody.

9. A method of detecting the presence or level of a Gal1 polypeptide said method comprising obtaining a sample and detecting said polypeptide in a sample by use of the monoclonal antibody or antigen-binding fragment thereof, according to claim 1, optionally wherein the monoclonal antibody or antigen-binding fragment thereof forms a complex with a Gal1 polypeptide and the complex is detected in the form of an enzyme linked immunosorbent assay (ELISA), radioimmune assay (RIA), immunochemically, or using an intracellular flow assay.

10. A method for predicting the clinical outcome of a subject afflicted with a disorder associated with aberrant Gal1, the method comprising:
 a) determining the level of expression of Gal1 in a patient sample using the monoclonal antibody or antigen-binding fragment thereof, according to claim 1,
 b) determining the level of expression of Gal1 in a sample from a control subject having a good clinical outcome using the monoclonal antibody or antigen-binding fragment thereof, according to claim 1; and
 c) comparing the level of expression of Gal1 in the patient sample and in the sample from the control subject;
wherein a significantly higher level of expression in the patient sample as compared to the expression level in the sample from the control subject is an indication that the patient has a poor clinical outcome.

11. A method of assessing the efficacy of a therapy for a disorder associated with aberrant Gal1 in a subject, the method comprising comparing:
 a) the level of expression of Gal1 using the monoclonal antibody or antigen-binding fragment thereof, according to claim 1, in a first sample obtained from the subject prior to providing at least a portion of the therapy to the subject, and
 b) the level of expression of Gal1 in a second sample obtained from the subject following provision of the portion of the therapy using the monoclonal antibody or antigen-binding fragment thereof, according to claim 1,
wherein a significantly lower level of expression of Gal1 in the second sample, relative to the first sample, is an indication that the therapy is efficacious for inhibiting the disorder in the subject.

12. A method of assessing the efficacy of a test compound for inhibiting a disorder associated with aberrant Gal1 in a subject, the method comprising comparing:
 a) the level of expression of Gal1 using the monoclonal antibody or antigen-binding fragment thereof, according to claim 1, in a first sample obtained from the subject and exposed to the test compound; and
 b) the level of expression of Gal1 in a second sample obtained from the subject using the monoclonal antibody or antigen-binding fragment thereof, according to claim 1,
wherein the second sample is not exposed to the test compound, and a significantly lower level of expression of Gal1, relative to the second sample, is an indication that the test compound is efficacious for inhibiting the disorder in the subject, optionally wherein the first and second samples are portions of a single sample obtained from the subject or portions of pooled samples obtained from the subject.

13. A method for monitoring the progression of a disorder associated with aberrant Gal1 expression in a subject, the method comprising:

a) detecting in a subject sample at a first point in time the level of expression of Gal1 using the monoclonal antibody or antigen-binding fragment thereof, according to claim 1;
b) repeating step a) at a subsequent point in time; and
c) comparing the level of expression of said Gal1 detected in steps a) and b) to monitor the progression of the disorder in the subject, optionally wherein between the first point in time and the subsequent point in time, the subject has undergone treatment to ameliorate the disorder.

14. The method of claim 13, wherein the disorder is selected from the group consisting of classical Hodgkin lymphoma (cHL), anaplastic large cell lymphoma (ALCL), MLL-rearranged ALL, EBV-positive post-transplant lymphoproliferative disorder (PTLD), nasopharyngeal carcinoma, Kaposi's sarcoma, breast cancer, prostate cancer, lung cancer, pancreatic cancer, squamous cell carcinoma of the head and neck, hepatocellular carcinoma, melanoma, gastrointestinal cancer, thyroid papillary carcinoma, laryngeal squamous cell carcinoma, and cutaneous T-cell lymphoma.

15. The method of claim 13, wherein the sample comprises cells, serum, peritumoral tissue, and/or intratumoral tissue obtained from the subject.

16. The method of claim 13, wherein said significant increase comprises an at least two fold increase between the level of expression of Gal1 in the subject sample relative to the normal level of expression of Gal1 in the sample from the control subject.

17. The method of claim 13, wherein the subject is a human.

\* \* \* \* \*

SEQUENCE LISTING

```
<160> NUMBER OF SEQ ID NOS: 28

<210> SEQ ID NO 1
<211> LENGTH: 408
<212> TYPE: DNA
<213> ORGANISM: Homo sapiens

<400> SEQUENCE: 1
atggcttgtg gtctggtcgc cagcaacctg aatctcaaac ctggagagtg ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
tgcaacagca aggacggcgg ggcctggggg accgagcagc gggaggctgt ctttcccttc     240
cagcctggaa gtgttgcaga ggtgtgcatc accttcgacc aggccaacct gaccgtcaag     300
ctgccagatg gatacgaatt caagttcccc aaccgcctca acctggaggc catcaactac     360
atggcagctg acggtgactt caagatcaaa tgtgtggcct ttgactga                 408

<210> SEQ ID NO 2
<211> LENGTH: 135
<212> TYPE: PRT
<213> ORGANISM: Homo sapiens

<400> SEQUENCE: 2

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
```

```
                  35                  40                  45
Arg Phe Asn Ala His Gly Asp Ala Asn Thr Ile Val Cys Asn Ser Lys
 50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                 85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130                 135

<210> SEQ ID NO 3
<211> LENGTH: 408
<212> TYPE: DNA
<213> ORGANISM: Mus musculus

<400> SEQUENCE: 3
atggcctgtg gtctggtcgc cagcaacctg aatctcaaac ctggggaatg tctcaaagtt      60
cggggagagg tggcctcgga cgccaagagc tttgtgctga acctgggaaa agacagcaac     120
aacctgtgcc tacacttcaa tcctcgcttc aatgcccatg agacgccaa caccattgtg      180 tgtaacacca aggaagatgg gacctgggga accgaacacc gggaacctgc cttcccttc      240 cagcccggga gcatcacaga ggtgtgcatc acctttgacc aggctgacct gaccatcaag     300
ctgccagacg gacatgaatt caagttcccc aaccgcctca acatggaggc catcaactac     360
atggcggcgg atgagacttc aagattaag tgcgtggcct ttgagtga                   408

<210> SEQ ID NO 4
<211> LENGTH: 135
<212> TYPE: PRT
<213> ORGANISM: Mus musculus

<400> SEQUENCE: 4

Met Ala Cys Gly Leu Val Ala Ser Asn Leu Asn Leu Lys Pro Gly Glu
 1               5                  10                  15

Cys Leu Lys Val Arg Gly Glu Val Ala Ser Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Thr Lys
 50                  55                  60

Glu Asp Gly Thr Trp Gly Thr Glu His Arg Glu Pro Ala Phe Pro Phe
65                  70                  75                  80

Gln Pro Gly Ser Ile Thr Glu Val Cys Ile Thr Phe Asp Gln Ala Asp
                 85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
        115                 120                 125

Ile Lys Cys Val Ala Phe Glu
        130                 135

<210> SEQ ID NO 5
```

<211> LENGTH: 132
<212> TYPE: PRT
<213> ORGANISM: Artificial Sequence
<220> FEATURE:
<223> OTHER INFORMATION: /note="Description of Artificial Sequence: 8A12 vK amino acid sequence"

<400> SEQUENCE: 5

```
Met Met Ser Pro Ala Gln Phe Leu Phe Leu Leu Val Leu Trp Ile Gln
1               5                   10                  15
Lys Thr Asn Gly Asp Val Val Met Thr Gln Thr Pro Leu Thr Leu Ser
            20                  25                  30
Val Thr Ile Gly Gln Pro Ala Ser Ile Ser Cys Lys Ser Ser Gln Ser
        35                  40                  45
Leu Leu Asp Ser Asp Gly Lys Thr Tyr Leu Asn Trp Leu Leu Gln Arg
    50                  55                  60
Pro Gly Gln Ser Pro Lys Arg Leu Ile Tyr Leu Ser Lys Leu Asp
65                  70                  75                  80
Ser Gly Val Pro Asp Arg Phe Thr Gly Ser Gly Ser Gly Thr Asp Phe
                85                  90                  95
Thr Leu Gln Ile Ser Arg Val Glu Ala Glu Asp Leu Gly Phe Tyr Tyr
            100                 105                 110
Cys Trp Gln Gly Thr His Phe Pro Tyr Thr Phe Gly Gly Gly Thr Lys
        115                 120                 125
Leu Glu Ile Lys
    130
```

<210> SEQ ID NO 6
<211> LENGTH: 336
<212> TYPE: DNA
<213> ORGANISM: Artificial Sequence
<220> FEATURE:
<223> OTHER INFORMATION: /note="Description of Artificial Sequence: 8A12 vK cDNA sequence"

<400> SEQUENCE: 6

```
atgatgagtc ctgcccagtt cctgtttctg ttagtgctct ggattcagaa aaccaacggt    60
gatgttgtga tgactcagac cccactcact tgtcggtta ccattggaca accagcctcc   120
atctcttgca gtcaagtca gagcctctta gatagtgatg gaaagacata tttgaattgg   180
ttgttacaga ggccaggcca gtctccaaag cgcctaatct atctgctgtc taaactggac   240
tctggagtcc ctgacaggtt cactggcagt ggatcaggga cagatttcac actgcaaatc   300
tacacgttcg gagggggac caagctggaa ataaaa                              336
```

<210> SEQ ID NO 7
<211> LENGTH: 131
<212> TYPE: PRT
<213> ORGANISM: Artificial Sequence
<220> FEATURE:
<223> OTHER INFORMATION: /note="Description of Artificial Sequence: 8A12 vH amino acid sequence"

<400> SEQUENCE: 7

```
Met Gly Trp Ser Gly Ile Phe Leu Phe Leu Leu Ser Val Thr Thr Gly
1               5                   10                  15
Val His Ser Gln Ala Tyr Leu Gln Gln Ser Gly Ala Glu Leu Val Arg
            20                  25                  30
Pro Gly Ala Ser Val Arg Met Ser Cys Lys Ala Ser Gly Tyr Thr Phe
        35                  40                  45
```

Thr Arg Tyr Asn Met His Trp Val Lys Gln Thr Pro Arg Gln Gly Leu
 50                  55                  60

Glu Trp Ile Gly Arg Ile Tyr Pro Gly Asn Gly Asp Thr Ser Tyr Asn
 65                  70                  75                  80

Gln Lys Phe Lys Gly Lys Ala Thr Leu Thr Val Asp Lys Ser Ser Ser
             85                  90                  95

Thr Ala Tyr Met Gln Leu Ser Ser Leu Thr Ser Glu Asp Ser Ala Val
             100                 105                 110

Tyr Phe Cys Thr Val Trp Asp Tyr Trp Gly Gln Gly Thr Thr Leu Thr
             115                 120                 125

Val Ser Ser
    130

<210> SEQ ID NO 8
<211> LENGTH: 393
<212> TYPE: DNA
<213> ORGANISM: Artificial Sequence
<220> FEATURE:
<223> OTHER INFORMATION: /note="Description of Artificial Sequence: 8A12
    vH cDNA sequence"

<400> SEQUENCE: 8
atgggatgga gcgggatctt tctcttcctc ctgtcagtaa ctacaggtgt ccactcccag      60
gcttatctac agcagtctgg ggctgagctg gtgaggcctg gggcctcagt gaggatgtcc     120
tgcaaggctt ctggctacac tttcaccagg tacaatatgc actgggtaaa gcagacacct     180
agacagggcc tggaatggat tggacgtatt tatccaggaa atggtgatac ttcctacaat     240
cagaagttca agggcaaggc cacactgact gtagacaaat cctccagcac agcctacatg     300
cagctcagca gcctgacatc tgaagactct gcggtctatt tctgtacagt ctgggactac     360
tggggccaag gcaccactct cacagtctcc tca                                  393

<210> SEQ ID NO 9
<211> LENGTH: 60
<212> TYPE: DNA
<213> ORGANISM: Artificial Sequence
<220> FEATURE:
<223> OTHER INFORMATION: /note="Description of Artificial Sequence: 8A12
    vK signal peptide cDNA sequence"

<400> SEQUENCE: 9
atgatgagtc ctgcccagtt cctgtttctg ttagtgctct ggattcagaa aaccaacggt      60

<210> SEQ ID NO 10
<211> LENGTH: 69
<212> TYPE: DNA
<213> ORGANISM: Artificial Sequence
<220> FEATURE:
<223> OTHER INFORMATION: /note="Description of Artificial Sequence: 8A12
    vK framework 1 cDNA sequence"

<400> SEQUENCE: 10
gatgttgtga tgactcagac cccactcact ttgtcggtta ccattggaca accagcctcc      60
atctcttgc                                                             69

<210> SEQ ID NO 11
<211> LENGTH: 48
<212> TYPE: DNA
<213> ORGANISM: Artificial Sequence
<220> FEATURE:
<223> OTHER INFORMATION: /note="Description of Artificial Sequence: 8A12
    vK CDR-L1 cDNA sequence"

<400> SEQUENCE: 11
aagtcaagtc agagcctctt agatagtgat ggaaagacat atttgaat        48

<210> SEQ ID NO 12
<211> LENGTH: 16
<212> TYPE: PRT
<213> ORGANISM: Artificial Sequence
<220> FEATURE:
<223> OTHER INFORMATION: /note="Description of Artificial Sequence: 8A12
      vK CDR-L1 amino acid sequence"

<400> SEQUENCE: 12

Lys Ser Ser Gln Ser Leu Leu Asp Ser Asp Gly Lys Thr Tyr Leu Asn
1               5                   10                  15

<210> SEQ ID NO 13
<211> LENGTH: 45
<212> TYPE: DNA
<213> ORGANISM: Artificial Sequence
<220> FEATURE:
<223> OTHER INFORMATION: /note="Description of Artificial Sequence: 8A12
      vK framework 2 cDNA sequence"

<400> SEQUENCE: 13
tggttgttac agaggccagg ccagtctcca aagcgcctaa tctat        45

<210> SEQ ID NO 14
<211> LENGTH: 21
<212> TYPE: DNA
<213> ORGANISM: Artificial Sequence
<220> FEATURE:
<223> OTHER INFORMATION: /note="Description of Artificial Sequence: 8A12
      vK CDR-L2 cDNA sequence"

<400> SEQUENCE: 14
ctgctgtcta aactggactc t        21

<210> SEQ ID NO 15
<211> LENGTH: 7
<212> TYPE: PRT
<213> ORGANISM: Artificial Sequence
<220> FEATURE:
<223> OTHER INFORMATION: /note="Description of Artificial Sequence: 8A12
      vK CDR-L2 amino acid sequence"

<400> SEQUENCE: 15

Leu Leu Ser Lys Leu Asp Ser
1               5

<210> SEQ ID NO 16
<211> LENGTH: 96
<212> TYPE: DNA
<213> ORGANISM: Artificial Sequence
<220> FEATURE:
<223> OTHER INFORMATION: /note="Description of Artificial Sequence: 8A12
      vK framework 3 cDNA sequence"

<400> SEQUENCE: 16
ggagtccctg acaggttcac tgcagtgga tcaggacag atttcacact gcaaatcagc        60
agagtggagg ctgaggattt gggatttat tattgc        96

<210> SEQ ID NO 17
<211> LENGTH: 27
<212> TYPE: DNA
<213> ORGANISM: Artificial Sequence
<220> FEATURE:
<223> OTHER INFORMATION: /note="Description of Artificial Sequence: 8A12
vK CDR-L3 cDNA sequence"

<400> SEQUENCE: 17
tggcaaggta cacattttcc ttacacg                                        27

<210> SEQ ID NO 18
<211> LENGTH: 9
<212> TYPE: PRT
<213> ORGANISM: Artificial Sequence
<220> FEATURE:
<223> OTHER INFORMATION: /note="Description of Artificial Sequence: 8A12
vK CDR-L3 amino acid sequence"

<400> SEQUENCE: 18

Trp Gln Gly Thr His Phe Pro Tyr Thr
1               5

<210> SEQ ID NO 19
<211> LENGTH: 30
<212> TYPE: DNA
<213> ORGANISM: Artificial Sequence
<220> FEATURE:
<223> OTHER INFORMATION: /note="Description of Artificial Sequence: 8A12
vK J segment cDNA sequence"

<400> SEQUENCE: 19
ttcggagggg ggaccaagct ggaaataaaa                                     30

<210> SEQ ID NO 20
<211> LENGTH: 57
<212> TYPE: DNA
<213> ORGANISM: Artificial Sequence
<220> FEATURE:
<223> OTHER INFORMATION: /note="Description of Artificial Sequence: 8A12
vH signal peptide cDNA sequence"

<400> SEQUENCE: 20
atgggatgga gcgggatctt tctcttcctc ctgtcagtaa ctacaggtgt ccactcc       57

<210> SEQ ID NO 21
<211> LENGTH: 90
<212> TYPE: DNA
<213> ORGANISM: Artificial Sequence
<220> FEATURE:
<223> OTHER INFORMATION: /note="Description of Artificial Sequence: 8A12
vH framework 1 cDNA sequence"

<400> SEQUENCE: 21
caggcttatc tacagcagtc tggggctgag ctggtgaggc ctggggcctc agtgaggatg    60
tcctgcaagg cttctggcta cactttcacc                                     90

<210> SEQ ID NO 22
<211> LENGTH: 15
<212> TYPE: DNA
<213> ORGANISM: Artificial Sequence
<220> FEATURE:
<223> OTHER INFORMATION: /note="Description of Artificial Sequence: 8A12
vH CDR-H1 cDNA sequence"

<400> SEQUENCE: 22
aggtacaata tgcac                                                     15

<210> SEQ ID NO 23
<211> LENGTH: 5

```
<212> TYPE: PRT
<213> ORGANISM: Artificial Sequence
<220> FEATURE:
<223> OTHER INFORMATION: /note="Description of Artificial Sequence: 8A12
      vH CDR-H1 amino acid sequence"

<400> SEQUENCE: 23

Arg Tyr Asn Met His
1               5

<210> SEQ ID NO 24
<211> LENGTH: 42
<212> TYPE: DNA
<213> ORGANISM: Artificial Sequence
<220> FEATURE:
<223> OTHER INFORMATION: /note="Description of Artificial Sequence: 8A12
      vH framework 2 cDNA sequence"

<400> SEQUENCE: 24
tgggtaaagc agacacctag acagggcctg gaatggattg ga                          42

<210> SEQ ID NO 25
<211> LENGTH: 51
<212> TYPE: DNA
<213> ORGANISM: Artificial Sequence
<220> FEATURE:
<223> OTHER INFORMATION: /note="Description of Artificial Sequence: 8A12
      vH CDR-H2 cDNA sequence"

<400> SEQUENCE: 25
cgtatttatc caggaaatgg tgatacttcc tacaatcaga agttcaaggg c                 51

<210> SEQ ID NO 26
<211> LENGTH: 17
<212> TYPE: PRT
<213> ORGANISM: Artificial Sequence
<220> FEATURE:
<223> OTHER INFORMATION: /note="Description of Artificial Sequence: 8A12
      vH CDR-H2 amino acid sequence"

<400> SEQUENCE: 26

Arg Ile Tyr Pro Gly Asn Gly Asp Thr Ser Tyr Asn Gln Lys Phe Lys
1               5                   10                  15

Gly

<210> SEQ ID NO 27
<211> LENGTH: 96
<212> TYPE: DNA
<213> ORGANISM: Artificial Sequence
<220> FEATURE:
<223> OTHER INFORMATION: /note="Description of Artificial Sequence: 8A12
      vH framework 3 cDNA sequence"

<400> SEQUENCE: 27
aaggccacac tgactgtaga caaatcctcc agcacagcct acatgcagct cagcagcctg       60
acatctgaag actctgcggt ctatttctgt acagtc                                 96

<210> SEQ ID NO 28
<211> LENGTH: 33
<212> TYPE: DNA
<213> ORGANISM: Artificial Sequence
<220> FEATURE:
<223> OTHER INFORMATION: /note="Description of Artificial Sequence: 8A12
      vH J segment cDNA sequence"
```

```
<400> SEQUENCE: 28
tggggccaag gcaccactct cacagtctcc tca                               33
```